United States Patent
Vo et al.

(10) Patent No.: US 12,426,938 B2
(45) Date of Patent: Sep. 30, 2025

(54) LOW PROFILE ELECTRODES FOR A SHOCK WAVE CATHETER

(71) Applicant: Shockwave Medical, Inc., Santa Clara, CA (US)

(72) Inventors: Khanh Vo, Santa Clara, CA (US); Jonathan Gallego, Santa Clara, CA (US); Huy Phan, Santa Clara, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 1030 days.

(21) Appl. No.: 16/993,114

(22) Filed: Aug. 13, 2020

(65) Prior Publication Data

US 2021/0085383 A1    Mar. 25, 2021

Related U.S. Application Data

(60) Provisional application No. 62/904,839, filed on Sep. 24, 2019.

(51) Int. Cl.
*A61B 17/22* (2006.01)
*A61B 18/12* (2006.01)
(Continued)

(52) U.S. Cl.
CPC .......... *A61B 18/14* (2013.01); *A61B 18/1206* (2013.01); *A61B 2017/22025* (2013.01);
(Continued)

(58) Field of Classification Search
CPC ................ A61B 18/14; A61B 18/1206; A61B 2018/00077; A61B 2018/00083;
(Continued)

(56) References Cited

U.S. PATENT DOCUMENTS 2,916,647 A    12/1959  George
3,412,288 A    11/1968  Ostrander
(Continued)

FOREIGN PATENT DOCUMENTS

AU    2009313507 B2    11/2014
AU    2013284490 B2    5/2018
(Continued)

OTHER PUBLICATIONS

Extended European Search Report received for European Patent Application No. 22196987.6, mailed on Dec. 8, 2022, 7 pages.
(Continued)

*Primary Examiner* — Darwin P Erezo
*Assistant Examiner* — Erin L Colello
(74) *Attorney, Agent, or Firm* — Morrison & Foerster LLP

(57) ABSTRACT

The present invention provides a system and method for treating tight, hard-to-cross calcified lesions in which an angioplasty balloon is used to dilate the lesions and provide shock waves to restore normal blood flow in a patient's artery. An exemplary device includes an elongated tube and a balloon wrapped circumferentially around the tube and sealed to a distal end of the tube. During treatment, the device is advanced into a patient's vasculature and the balloon is inflated with conductive fluid such that the balloon is fixed to walls of the vasculature proximal to the calcified lesion. The balloon includes at least one low-profile emitter positioned near the distal end of the balloon, which may be activated to generate shock waves to break loose calcifications in the lesion. After calcium in the tight lesion has been modified, the balloon can be deflated and advanced further into the lesion to continue treatment.

18 Claims, 14 Drawing Sheets

(51) Int. Cl.
*A61B 18/14* (2006.01)
*A61B 18/00* (2006.01)

(52) U.S. Cl.
CPC .............. *A61B 2018/00077* (2013.01); *A61B 2018/00083* (2013.01); *A61B 2018/0022* (2013.01); *A61B 2018/00422* (2013.01); *A61B 2018/1467* (2013.01)

(58) Field of Classification Search
CPC .. A61B 2018/0022; A61B 2018/00422; A61B 2018/1467; A61B 2018/1497; A61B 2018/162; A61B 2017/22025; A61B 2017/22062; A61B 17/225; A61B 17/22004; A61B 17/22012; A61B 17/2202
See application file for complete search history.

(56) References Cited

U.S. PATENT DOCUMENTS

| | | |
|---|---|---|
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Doernhoefer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 * | 4/2001 | Chandrasekaran ... A61M 25/10 606/41 |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,138,249 B2 | 9/2015 | Adams et al. |
| 9,198,825 B2 | 12/2015 | Katragadda et al. |
| 9,237,984 B2 * | 1/2016 | Hawkins .......... A61B 17/22022 |
| 9,333,000 B2 | 5/2016 | Hakala et al. |
| 9,421,025 B2 | 8/2016 | Hawkins et al. |
| 9,433,428 B2 | 9/2016 | Hakala et al. |

(56) References Cited

U.S. PATENT DOCUMENTS

| | | |
|---|---|---|
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,959,743 B2 | 3/2021 | Adams et al. |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,534,187 B2 | 12/2022 | Bonutti |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 11,779,363 B2 * | 10/2023 | Vo ................... A61B 17/2202 606/128 |
| 12,232,752 B2 | 2/2025 | Nguyen et al. |
| 2001/0041880 A1 * | 11/2001 | Brisken ................ A61N 7/022 604/503 |
| 2001/0044596 A1 | 11/2001 | Jaafar |
| 2002/0045890 A1 | 4/2002 | Brisken et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0221013 A1 | 8/2012 | Hawkins et al. |
| 2012/0253358 A1 | 10/2012 | Golan et al. |
| 2013/0030431 A1 | 1/2013 | Adams |
| 2013/0030447 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0005576 A1 | 1/2014 | Adams et al. |
| 2014/0039513 A1 | 2/2014 | Hakala et al. |
| 2014/0046229 A1 | 2/2014 | Hawkins et al. |
| 2014/0052145 A1 | 2/2014 | Adams et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |
| 2014/0214061 A1 | 7/2014 | Adams et al. |
| 2014/0243820 A1 | 8/2014 | Adams et al. |
| 2014/0243847 A1 | 8/2014 | Hakala et al. |
| 2014/0288570 A1 | 9/2014 | Adams |
| 2015/0073430 A1 | 3/2015 | Hakala et al. |
| 2015/0238208 A1 | 8/2015 | Adams et al. |
| 2015/0320432 A1 | 11/2015 | Adams et al. |
| 2016/0151081 A1 | 6/2016 | Adams et al. |
| 2016/0183957 A1 | 6/2016 | Hakala et al. |
| 2016/0324534 A1 | 11/2016 | Hawkins et al. |
| 2016/0331389 A1 | 11/2016 | Hakala et al. |
| 2017/0135709 A1 | 5/2017 | Nguyen et al. |
| 2018/0256250 A1 | 9/2018 | Adams et al. |
| 2018/0360482 A1 * | 12/2018 | Nguyen ................ A61M 5/007 |
| 2019/0069916 A1 | 3/2019 | Hawkins et al. |
| 2019/0150960 A1 * | 5/2019 | Nguyen ............ A61B 18/1492 |
| 2020/0085458 A1 | 3/2020 | Nguyen et al. |
| 2020/0297366 A1 | 9/2020 | Nguyen et al. |
| 2020/0383724 A1 | 12/2020 | Adams et al. |
| 2021/0282792 A1 | 9/2021 | Adams et al. |
| 2021/0338258 A1 | 11/2021 | Hawkins et al. |
| 2022/0015785 A1 | 1/2022 | Hakala et al. |
| 2022/0240958 A1 | 8/2022 | Nguyen et al. |
| 2023/0043475 A1 | 2/2023 | Adams |
| 2023/0293197 A1 | 9/2023 | Nguyen et al. |
| 2023/0310073 A1 | 10/2023 | Adams et al. |
| 2023/0329731 A1 | 10/2023 | Hakala et al. |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |

(56) References Cited

FOREIGN PATENT DOCUMENTS

| | | |
|---|---|---|
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| CN | 104519809 A | 4/2015 |
| CN | 104540459 A | 4/2015 |
| CN | 104582597 A | 4/2015 |
| CN | 104582621 A | 4/2015 |
| CN | 105030325 A | 11/2015 |
| CN | 109788965 A | 5/2019 |
| DE | 3038445 A1 | 5/1982 |
| DE | 202006014285 U1 | 12/2006 |
| EP | 442199 A2 | 8/1991 |
| EP | 571306 A1 | 11/1993 |
| EP | 623360 A1 | 11/1994 |
| EP | 647435 A1 | 4/1995 |
| EP | 2253884 A1 | 11/2010 |
| EP | 2362798 B1 | 4/2014 |
| JP | 62-99210 U | 6/1987 |
| JP | 62-275446 A | 11/1987 |
| JP | 3-63059 A | 3/1991 |
| JP | 6-125915 A | 5/1994 |
| JP | H06-506373 A | 7/1994 |
| JP | 7-47135 A | 2/1995 |
| JP | H8-89511 A | 4/1996 |
| JP | 10-99444 A | 4/1998 |
| JP | 10-314177 A | 12/1998 |
| JP | 10-513379 A | 12/1998 |
| JP | 2002-538932 A | 11/2002 |
| JP | 2004081374 | 3/2004 |
| JP | 2004-357792 A | 12/2004 |
| JP | 2008-506447 A | 12/2004 |
| JP | 2011-513694 A | 12/2004 |
| JP | 2011-520248 A | 12/2004 |
| JP | 2005-501597 A | 1/2005 |
| JP | 2005-95410 A | 4/2005 |
| JP | 2005-515825 A | 6/2005 |
| JP | 2006-516465 A | 7/2006 |
| JP | 2007-532182 A | 11/2007 |
| JP | 2007289707 A | 11/2007 |
| JP | 2011-524203 A | 9/2011 |
| JP | 2011-528963 A | 12/2011 |
| JP | 2012505050 A | 3/2012 |
| JP | 2012-508042 A | 4/2012 |
| JP | 2015522344 A | 8/2015 |
| JP | 2015525657 A | 9/2015 |
| JP | 2015528327 A | 9/2015 |
| JP | 6029828 B2 | 11/2016 |
| JP | 6081510 B2 | 2/2017 |
| WO | WO89/11307 | 11/1989 |
| WO | WO96/24297 | 8/1996 |
| WO | WO99/00060 | 1/1999 |
| WO | WO99/02096 | 1/1999 |
| WO | WO 00/56237 | 9/2000 |
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 * | 10/2009 ............ A61B 18/14 |
| WO | WO-2009126544 A1 | 10/2009 |
| WO | WO-2009136268 A1 | 11/2009 |
| WO | WO-2009152352 A2 | 12/2009 |
| WO | WO-2010014515 A2 | 2/2010 |
| WO | WO-2010054048 A2 | 5/2010 |
| WO | WO-2010054048 A3 | 9/2010 |
| WO | WO-2011006017 A1 | 1/2011 |
| WO | WO-2011094111 A2 | 8/2011 |
| WO | WO-2011143468 A2 * | 11/2011 ......... A61B 1/00082 |
| WO | WO-2012025833 A2 | 3/2012 |
| WO | WO-2013059735 A1 | 4/2013 |
| WO | WO-2014025397 A1 | 2/2014 |
| WO | WO-2014025620 A1 | 2/2014 |
| WO | WO-2015017499 A1 | 2/2015 |
| WO | WO-2019099218 A1 | 5/2019 |

OTHER PUBLICATIONS

Non-Final Office Action received for U.S. Appl. No. 16/893,400, mailed on Aug. 1, 2022, 9 pages.
Notice of Allowance received for European Patent Application No. 18804877.1, mailed on May 27, 2022, 5 pages.
Summons to attend oral proceedings received for European Patent Application No. 18804877.1 mailed on Dec. 23, 2021, 7 pages.
21 C.F.R. 870.5100 Title 21, vol. 8 Apr. 1, 2018 pp. 1-2.
Abraham et al. (1992). "Effect of Humidity and on the dc Breakdown and Rod-Plane Temperature of Rod-Rod Gaps," IEEE Transactions on Electrical Insulation, 27(2):207-213.
Advisory Action received for U.S. Appl. No. 13/615,107, mailed on Nov. 6, 2015, 3 pages.
Advisory Action received for U.S. Appl. No. 12/482,995, mailed on Jun. 2, 2014, 3 pages.
Advisory Action received for U.S. Appl. No. 12/482,995, mailed on Sep. 29, 2011, 2 pages.
Advisory Action received for U.S. Appl. No. 12/581,295, mailed on Jul. 3, 2014, 3 pages.
Advisory Action received for U.S. Appl. No. 13/049,199, mailed on Jun. 7, 2012, 3 pages.
Advisory Action received for U.S. Appl. No. 13/267,383, mailed on Jan. 6, 2014, 4 pages.
Allen et al. (1993). "Dielectric Breakdown in Nonuniform Field Air Gaps: Ranges of Applicability to dc Voltage Measurement," IEEE Transactions on Electrical Insulation, 28(2):183-191.
Allibone et al. (1972). "Influence of Humidity on the Breakdown of Sphere and Rod Gaps Under Impulse Voltages of Short and Long Wavefronts," Proceedings of the Institution of Electrical Engineers, 119(9):1417-1422.
Amendment After Final Action received for U.S. Appl. No. 12/482,995, filed May 16, 2014, 8 pages.
Amendment in Response to Non-Final Office Action received for U.S. Appl. No. 12/482,995, filed Jan. 9, 2014 Jan. 9, 2014, 9 pages.
Amighi et al., (2005). "Impact of the Rapid-Exchange Versus Over-the-Wire Technique on Procedural Complications of Renal Artery Angioplasty," J Endovasc Ther., 12:233-239.
Anvari et al. (1973). "Study of a 40 KV Multistage Spark Gap Operated in Air at Atmospheric Pressure," Journal of Physics E: Scientific Instruments, 6:113-115.
Armstrong, Ehrin Responses to Question 6 by Patent Owner's Declarants Ehrin Armstrong, Jan. 29, 2020, 5 pages.
Armstrong, Ehrin Responses to Questions 1-5 by Patent Owner's Declarants Ehrin Armstrong, Jan. 24, 2020, 4 pages.
Athanasoulis, (1980). "Percutaneous Transluminal Angioplasty: General Principles," American journal of Roentgenology, 135:893-900.
Bank of America Merrill Lynch A Simple Solution to a Difficult (and Large) Problem—Initiating Coverage of SWAV Shockwave Medical Inc., Apr. 1, 2019, pp. 1-22.
Becker et al., (1988). "Radiofrequency Balloon Angioplasty," Rationale and Proof of Principle Investigative Radiology, 23(11):810-817.
Belmouss (2015). "Effect of Electrode Geometry on High Energy Spark Discharges in Air," Purdue University Open Access Theses, 216 pages.
Ben-Dor et al., "Handbook of Shock Waves", Shockwave Medical, Inc. Patent Owner Exhibit 2223, vol. 2, 2001, 824 pages.
Bittl et al. (1993). "Publication Information—Coronary Artery Perforation during Excimer Laser Coronary Angioplasty," Journal of the American College of Cardiology, 21(5):1-6.
Bittl et al., (1993). "Coronary Artery Perforation during Excimer Laser Coronary Angioplasty," Journal of the American College of Cardiology, 21(5):1158-1165.
Brace et al. (2009). "Pulmonary Thermal Ablation: Comparison of Radiofrequency and Microwave Devices by Using Gross Pathologic and CT Findings in a Swine Model," Radiology, 251(3):705-711.

(56) References Cited

OTHER PUBLICATIONS

Brinton et al., (2016). "Publication Information—TCT-777 Safety and Performance of the Shockwave Medical Lithoplasty® System in Treating Calcified Peripheral Vascular Lesions: 6-Month Results from the Two-Phase Disrupt Pad Study," Journal of the American College of Cardiology, 68(18):1-5.
Brinton et al., (2016). "TCT-777 Safety and Performance of the Shockwave Medical Lithoplasty® System in Treating Calcified Peripheral Vascular Lesions: 6-Month Results from the Two-Phase Disrupt Pad Study," Journal of the American College of Cardiology, 68(18):B314.
Brodmann et al., (2018). "Primary outcomes and mechanism of action of intravascular lithotripsy in calcified femoropopliteal lesions: Results of the Disrupt Pad II Catheter ," Cardiovasc Interv., 93(2):335-342.
Calcium in the Peripheral and Coronary Arteries: The Pathologist View, Deposition Exhibit from Deposition of Dr. Finn, Mar. 6, 2020, 27 pages.
Canfield et al., (2018). "40 Years of Percutaneous Coronary Intervention: History and Future Directions," Journal of Personalized Medicine, 8(33):1-9.
Cardiology Today's Intervention, "Shockwave Attracts Additional Investment from Abiomed, has IPO," Available Online at <https://www.healio.com/cardiac-vascular-intervention/peripheral/news/online/%7Bf96c1e20-b4a9-4167-bdb8-254e86a8182a%7D/shockwave-attracts-additional-investment-from-abiomed-has-ipo>, Mar. 12, 2019, pp. 1-2.
Chart of Mantell Detailed Mapping of Provisional to '371 Claims Case No. IPR2019-00405 2020, 12 pages.
Cleveland et al. (2000). "Design and Characterization of a Research Electrohydraulic Lithotripter Patterned after the Dornier HM3," Review of Scientific Instruments, 71(6):2514-2525.
Cleveland et al. (2000). "Publication Information—Design and Characterization of a Research Electrohydraulic Lithotripter Patterned after the Dornier HM3," Review of Scientific Instruments, 71, No. 6, 4 pages.
Cleveland et al., (2012). "The Physics of Shock Wave Lithotripsy", Extracorporeal Shock Wave Lithotripsy, Part IV, Chapter 38, pp. 317-332.
Concise Description of Relevance Accompanying Third Party Preissuance Submission Under 37 CFR 1.290 for U.S. Appl. No. 15/817,073, filed Aug. 5, 2019, 31 pages.
Concise Description of Relevance Accompanying Third Party Preissuance Submission Under 37 CFR 1.290 for U.S. Appl. No. 16/028,225, filed Aug. 2, 2019, 4 pages.
Concise Description of Relevance Accompanying Third Party Preissuance Submission Under 37 CFR 1.290 U.S. Appl. No. 16/240,556, filed Sep. 20, 2019, 14 pages.
Connors et al., (2003). "Renal Nerves Mediate Changes in Contralateral Renal Blood Flow after Extracorporeal Shockwave Lithotripsy", Nephron Physiology, vol. 95, pp. 67-75.
Corrected Notice of Allowance received for U.S. Appl. No. 16/544,516, mailed on May 26, 2020, 5 pages.
Das et al., (2014). "Technique Optimization of Orbital Atherectomy in Calcified Peripheral Lesions of the Lower Extremities," Catheterization and Cardiov Interv, 83:115-122.
Deagon (2019). "Technology—Shockwave Medical IPO Soars On First Day Of Trading," Investor's Business Daily, Available Online at <https://www.investors.com/news/technology/shockwave-medical-ipo-soars-trading/>, pp. 1-15.
Decision Instituting Inter Partes Review for U.S. Pat. No. 8,956,371, by the Patent Trial and Appeal Board dated Jul. 9, 2019, 28 pages.
Decision Instituting Inter Partes Review of U.S. Pat. No. 9,642,673, by the Patent Trial and Appeal Board dated Jul. 22, 2019, 22 pages.
Decision of Appeals Notice received for Japanese Patent Application No. 2011-534914, mailed on Oct. 17, 2016, 2 pages of Official Copy only.
Decision to Grant received for European Patent Application No. 13756766.5, mailed on May 27, 2016, 2 pages.
Decision to Grant received for European Patent Application No. 09763640.1, mailed on Feb. 22, 2018, 2 pages.
Decision to Grant received for European Patent Application No. 09825393.3, mailed on Mar. 13, 2014, 2 pages.
Decision to Grant received for European Patent Application No. 13827971.6, mailed on Jan. 31, 2019, 2 pages.
Decision to Grant received for Japanese Patent Application No. 2011-513694, mailed on Oct. 7, 2014, 3 pages (Official Copy Only) (See Communication under 37 CFR § 1.98(a) (3)).
Declaration and CV of Aloke V. Finn Case IPR2019-00405 Feb. 20, 2020, 45 pages.
Declaration and CV of Jeffrey Chambers Case IPR2019-00405 Feb. 19, 2020, 32 pages.
Declaration of Dr. Morten Olgaard Jensen, Dec. 6, 2018, pp. 1-113.
Declaration of Juanita DeLoach Exhibit 1236, Case IPR2019-00408 Feb. 18, 2020, 4 pages.
Declaration of Natalie J. Grace dated Apr. 10, 2019, pp. 1-3.
Declaration of William Patrick Stephens, Apr. 22, 2019, pp. 1-6.
Deposition Exhibit from Deposition of Dr. Jensen, Balloon Attributes that Impact Deliverability, Mar. 4, 2020, 1 page.
Deposition Exhibit from Deposition of Dr. Jensen, Diagram from Wikipedia Page for Balloon Catheters, Mar. 4, 2020, 1 page.
Deposition Exhibit from Deposition of Dr. Jensen, Figures 1 and 2 of JP Patent No. 62-275446 (color added), Mar. 4, 2020, 1 page.
Deposition Exhibit from Deposition of Dr. Jensen, Handwritten Diagram, Mar. 4, 2020, 1 page.
Deposition Transcript (compressed) of Dr. Aloke Finn, Case No. IPR2019-00405, Mar. 6, 2020, 31 pages.
Deposition Transcript (compressed) of Dr. Daniel van der Weide, Case No. IPR2019-00409, U.S. Pat. No. 8,728,091 B2, Jan. 10, 2020., 111 pages.
Deposition Transcript (compressed) of Dr. Jeffrey Chambers, Case No. IPR2019-00405, Mar. 2, 2020., 81 pages.
Deposition Transcript (compressed) of Dr. Morten Olgaard Jensen, Case No. IPR2019-00405, U.S. Pat. No. 8,956,371, Mar. 4, 2020, 73 pages.
Deposition Transcript (compressed) of Dr. Morten Olgaard Jensen, Case No. IPR2019-00408, U.S. Pat. No. 9,642,673, Feb. 26, 2020., 80 pages.
Deposition Transcript (compressed) of Ronald David Berger Case No. IPR2019-00405 Jan. 27, 2020, 103 pages.
Dewhirst et al., (2003). "Basic Principles of Thermal Dosimetry and Thermal Thresholds for Tissue Damage from Hyperthermia International," Journal of Hyperthermia, 19(3):267-294.
Dewhirst et al., (2003). "Publication Information—Basic Principles of Thermal Dosimetry and Thermal Thresholds for Tissue Damage from Hyperthermia," International Journal of Hyperthermia, 19(3):1-3.
Diamondback 360® Peripheral Orbital Atherectomy System, Cardiovascular Systems, Inc., Patent Owner Exhibit 2231, 2019, 58 pages.
Dodd, (1842). "Two Cases of Calculus in the Bladder, in Which Lithotripsy Was Performed," Provincial Medical & Surgical Journal, 3(71):368-370.
Dodge Jr., et al., (1992). "Lumen Diameter of Normal Human Coronary Arteries," Influence of Age, Sex, Anatomic Variation, and Left Ventricular Hypertrophy or Dilation Circulation, 86(1):232-246.
Drilling Research on the Electrical Detonation and Subsequent Cavitation in a Liquid Technique (Spark Drilling), Drilling Research Division-5718, Sandia Laboratories, Status Report Jul. 1-Dec. 31, 1975, 53 pages.
E-mail from Cook Alciati to Mark Nelson confirming Dr. Chamber's total compensation amount from *Cardiovascular Systems, Inc, CSI v. Shockwave*—Dr. Chambers Testimony, Mar. 20, 2020, 1 page.
Extended European Search Report (includes Supplementary European Search Report and Search Opinion) received for European Patent Application No. 09763640.1, mailed on Oct. 10, 2013, 5 pages.
Extended European Search Report and Search Opinion received for European Patent Application No. 09825393.3, mailed on Feb. 28, 2013, 6 pages.

(56) References Cited

OTHER PUBLICATIONS

Extended European Search Report received for European Patent Application No. 13827971.6, mailed on Apr. 12, 2016, 8 pages.
Farb et al., (2002). "Morphological Predictors of Restenosis After Coronary Stenting in Humans," Circulation, pp. 2974-2980.
FDA Clears Lithoplasty Balloon That Shatters Calcified Lesions With Ultrasound Diagnostic and Interventional Cardiology, Available Online at <https://www.dicardiology.com/product/fda-clearslithoplasty-balloon-shatters-calcified-lesions-ultrasound> Sep. 16, 2016, pp. 1-5.
Fernandes et al., (2007). "Enhanced infarct border zone function and altered mechanical activation predict inducibility of monomorphic ventricular tachycardia in patients with ischemic cardiomyopathy," Radiology, 245(3):712-719.
File History for U.S. Pat. No. 9,642,673, May 9, 2017, pp. 1-1789.
File History of U.S. Pat. No. 8,956,371, pp. 1-1561.
Final Office Action received for U.S. Appl. No. 12/482,995, mailed on Jul. 22, 2011, 14 pages.
Final Office Action received for U.S. Appl. No. 12/611,997, mailed on Dec. 11, 2012, 9 pages.
Final Office Action received for U.S. Appl. No. 12/611,997, mailed on Nov. 10, 2011, 15 pages.
Final Office Action received for U.S. Appl. No. 13/049,199, mailed on Apr. 4, 2012, 10 pages.
Final Office Action received for U.S. Appl. No. 13/207,381, mailed on Nov. 2, 2012, 7 pages.
Final Office Action received for U.S. Appl. No. 14/271,342 mailed on Feb. 27, 2015, 7 pages.
Final Office Action received for U.S. Appl. No. 12/482,995, mailed on Feb. 20, 2014, 11 pages.
Final Office Action received for U.S. Appl. No. 12/581,295, mailed on Jun. 5, 2014, 14 pages.
Final Office Action received for U.S. Appl. No. 12/611,997, mailed on Oct. 24, 2013, 10 pages.
Final Office Action received for U.S. Appl. No. 13/049,199 mailed on Aug. 11, 2014, 8 pages.
Final Office Action received for U.S. Appl. No. 13/207,381, mailed on Nov. 7, 2013, 7 pages.
Final Office Action received for U.S. Appl. No. 13/267,383, mailed on May 28, 2015, 12 pages.
Final Office Action received for U.S. Appl. No. 13/267,383, mailed on Oct. 25, 2013, 8 pages.
Final Office Action received for U.S. Appl. No. 13/534,658, mailed on Aug. 23, 2016, 11 pages.
Final Office Action received for U.S. Appl. No. 13/615,107, mailed on Sep. 1, 2015, 9 pages.
Final Office Action received for U.S. Appl. No. 13/646,570, mailed on Dec. 23, 2014, 10 pages.
Final Office Action received for U.S. Appl. No. 14/229,735, mailed on Aug. 27, 2015, 7 pages.
Final Office Action received for U.S. Appl. No. 15/213,105, mailed on May 4, 2018, 8 pages.
Final Office Action received for U.S. Appl. No. 15/346,132, mailed on Jun. 5, 2019, 12 pages.
Final Office Action received for U.S. Appl. No. 15/979,182, mailed on Oct. 21, 2019, 6 pages.
Final Office Action received for U.S. Appl. No. 16/183,438, mailed on Aug. 11, 2020, 11 pages.
Final Office Action received for U.S. Appl. No. 14/660,539, mailed on Aug. 3, 2017, 11 pages.
Final Written Decision *Ariosa Diagnostics Inc.* vs. *Illumina Inc.* dated Jan. 7, 2016, pp. 1-18.
Final Written Decision for U.S. Pat. No. 8,956,371, by the Patent Trial and Appeal Board dated Jul. 8, 2020, 89 pages.
Fung (1993). "Biomechanics—Mechanical Properties of Living Tissues," Second Edition, Springer, 14 pages.
Gambihler et al., (1994). "Permeabilization of the Plasma Membrane of Ll210 Mouse Leukemia Cells Using Lithotripter Shock Waves," The Journal of Membrane Biology, 141:267-275.
Gottlieb (2018). "U.S. Department of Health and Human Services, Food and Drug Administration Report to Congress by Scott Gottlieb," Exhibit 1217, Sep. 30, 2018, 10 pages.
Grassi et al., (2012). "Novel Antihypertensive Therapies: Renal Sympathetic Nerve Ablation and Carotid Baroreceptor Stimulation," Curr Hypertens Rep, 14:567-572.
Grocela et al. (1997). "Intracorporeal Lithotripsy. Instrumentation and Development," Urologic Clinics of North America, 24(1):13-23.
Hawkins et al. U.S. Appl. No. 61/061,170, filed Jun. 13, 2008, titled "Shockwave Balloon Catheter System". pp. 1-50.
Hill, Jonathan M., Deposition Transcript (compressed) of Jonathan M. Hill, M.D. Exhibit 1211, Case No. IPR2019-00408, U.S. Pat. No. 9,642,673 Dec. 16, 2019, 63 pages.
Hodges et al., (1994). "Publication Information—Ultrasound Determination of Total Arterial Wall Thickness," Journal of Vascular Surgery, 19(4):1-13.
Hodges et al., (1994). "Ultrasound Determination of Total Arterial Wall Thickness," Journal of Vascular Surgery, 19(4):745-753.
Huang et al., (1998). "Cost Effectiveness of Electrohydraulic Lithotripsy v Candela Pulsed-Dye Laser in Management of the Distal Ureteral Stone," Journal of Endourology, 12(3):237-240.
Intention to Grant received for European Patent Application No. 09763640.1, mailed on Oct. 11, 2017, 8 pages.
Intention to Grant received for European Patent Application No. 13756766.5, mailed on Jan. 8, 2016, 5 pages.
Intention to Grant received for European Patent Application No. 13827971.6, mailed on Sep. 28, 2018, 8 pages.
International Preliminary Report on Patentability received for PCT Patent Application No. PCT/US2009/047070, mailed on Dec. 23, 2010, 7 pages.
International Preliminary Report on Patentability received for PCT Patent Application No. PCT/US2009/063354, mailed on May 19, 2011, 6 pages.
International Preliminary Report on Patentability received for PCT Patent Application No. PCT/US2011/047070, mailed on Feb. 21, 2013, 7 pages.
International Preliminary Report on Patentability received for PCT Patent Application No. PCT/US2012/023172, mailed on Aug. 15, 2013, 6 pages.
International Preliminary Report on Patentability received for PCT Patent Application No. PCT/US2012/063925, mailed on May 22, 2014, 12 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987, issued on Nov. 20, 2014, 11 pages.
International Preliminary Report on Patentability received for PCT Patent Application No. PCT/US2013/048277, mailed on Jan. 8, 2015, 9 pages.
International Preliminary Report on Patentability received for PCT Patent Application No. PCT/US2013/054104 mailed on Feb. 19, 2015, 8 pages.
International Preliminary Report on Patentability received for PCT Patent Application No. PCT/US2013/055431, mailed on Feb. 26, 2015, 7 pages.
International Preliminary Report on Patentability received for PCT Patent Application No. PCT/US2013/059533, mailed on Mar. 26, 2015, 10 pages.
International Preliminary Report on Patentability received for PCT Patent Application No. PCT/US2016/060817, mailed on May 31, 2018, 9 pages.
International Preliminary Report on Patentability received for PCT Patent Application No. PCT/US2018/059083, mailed on May 28, 2020, 6 pages.
International Search Report and Written Opinion Received for PCT Application No. PCT/US2018/059083, mailed on Jan. 22, 2019, 8 pages.
International Search Report and Written Opinion received for PCT Patent Application No. PCT/US2013/031805, mailed on May 20, 2013, 13 pages.

(56) References Cited

OTHER PUBLICATIONS

International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
International Search Report and Written Opinion received for PCT Patent Application No. PCT/US2015/029088 mailed on Jul. 16, 2015, 13 pages.
International Search Report and Written Opinion received for PCT Patent Application No. PCT/US2015/060453, mailed on Jan. 21, 2016, 15 pages.
International Search Report and Written Opinion received for PCT Patent Application No. PCT/US2016/060817, mailed on Feb. 20, 2017, 13 pages.
International Search Report and Written Opinion received for PCT Patent Application No. PCT/US2020/046134, mailed on Oct. 26, 2020, 18 pages.
International Search Report received for PCT Patent Application No. PCT/US2009/047070, mailed on Jan. 19, 2010, 4 pages.
International Search Report received for PCT Patent Application No. PCT/US2009/063354, mailed on Jun. 11, 2010, 3 pages.
International Search Report received for PCT Patent Application No. PCT/US2012/023172, mailed on Sep. 28, 2012, 3 pages.
International Written Opinion received for PCT Patent Application No. PCT/US2009/063354, mailed on Jun. 11, 2010, 4 pages.
International Written Opinion received for PCT Patent Application No. PCT/US2011/047070, mailed on May 1, 2012, 5 pages.
International Written Opinion received for PCT Patent Application No. PCT/US2012/023172, mailed on Sep. 28, 2012, 4 pages.
International Written Opinion received for PCT Patent Application No. PCT/US2009/047070, mailed on Jan. 19, 2010, 5 pages.
Jacob (1993). "Applications and Design with Analog Integrated Circuits," Second Edition, Prentice-Hall International Editions, pp. 1-8.
Jahnke et al., (2008). "Retrospective Study of Rapid-Exchange Monorail Versus Over-the-Wire Technique for Femoropopliteal Angioplasty," Cardiovascular and Interventional Radiology, 31:854-859.
Jensen, Morten O. "Supplemental Declaration of Dr. Morten Olgaard Jensen in Support of Petitioner's Reply," Case IPR2019-00408, U.S. Pat. No. 9,642,673 B2, Feb. 18, 2020, 54 pages.
Johnson et al. (1992). "Electric Circuit Analysis—Second Edition," Prentice-Hall International Editions, pp. 1-17.
Johnston et al., (2004). "Publication Information—Non-Newtonian Blood Flow in Human Right Coronary Arteries: Steady State Simulations," Journal of Biomechanics, 37(5):1-2.
Johnston et al., (2006). "Non-Newtonian Blood Flow in Human Right Coronary Arteries: Transient Simulations," Journal of Biomechanics, 39(6):1-35.
Kaplan et al., (1993). "Healing after Arterial Dilatation with Radiofrequency Thermal and Nonthermal Balloon Angioplasty Systems," Journal of Investigative Surgery, 6:33-52.
Kereiakes, Dean J. "Deposition Transcript (compressed) of Dean J. Kereiakes", Exhibit 1213, Cases No. 2019-00405, 00408 and 00409, Jan. 7, 2020., 65 pages.
Knuttinen et al., (2014). "Unintended Thermal Injuries from Radiofrequency Ablation: Organ Protection with An Angioplasty Balloon Catheter in an Animal Model," Journal of Clinical Imaging Science, 4(1):1-6.
Kodama et al., (2002). "Shock wave-mediated molecular delivery into cells," Biochimica et Biophysica Acta, 1542:186-194.
Laeseke et al. (2006). "Multiple-Electrode RF Ablation Creates Confluent Areas of Necrosis: Results in in vivo Porcine Liver," Radiology, 241(1):116-124.
Lauer et al., (1997). "Shock wave permeabilization as a new gene transfer method," Gene Therapy, 4:710-715.
Lee et al., (1991). "Structure-Dependent Dynamic Mechanical Behavior of Fibrous Caps From Human Atherosclerotic Plaques," Circulation, 83(5):1764-1770.
Lee et al., (2017). "Orbital atherectomy for treating de novo, severely calcified coronary lesions: 3-year results of the pivotal Orbit II trial," Cardiovascular Revascularization Medicine, 18:261-264.
Lee et al., (2018). "Acute Procedural Outcomes of Orbital Atherectomy for the Treatment of Profunda Femoris Artery Disease: Subanalysis of the Confirm Registries," J Invasive Cardio, 330(5):177-181.
Linnemeier et al., (1993). "Radiation Exposure: Comparison of Rapid Exchange and Conventional Over-the-Wire Coronary Angioplasty Systems," Catheterization and Cardiovascular Diagnosis, 30:11-14.
Lipowski, et al. U.S. Appl. No. 61/051,262 pp. 1-36.
Liu et al., (2015). "Current Understanding of Coronary Artery Calcification," Journal of Geriatric Cardiology, 12:668-675.
Llewellyn-Jones (1963). "The Mechanism of Electrode Erosion in Electrical Discharges," Platinum Metals Rev. vol. 7(2):58-65.
Loske (2007). "Shock Wave Physics for Urologists," Universidad Nacional Autónoma de México, 185 pages.
Mantell U.S. Appl. No. 61/051,262 20 pages.
Meraj et al., (2018). "Clinical outcomes of Atherectomy Prior to Percutaneous Coronary Intervention: A Comparison of Outcomes following Rotational Versus Orbital Atherectomy (COAP-PCI study)," Journal of Interventional Cardiology, 31:478-485.
Millman et al. (1987). "Microelectronics—Second Edition," McGraw-Hill International Editions, pp. 1-15.
Mills et al., (2019). "Cracking the Code on Calcium; Initiate with Buy, $39 Target Canaccord Genuity—Capital Markets," US Equity Research Apr. 1, 2019, pp. 1-63.
Mitomo, "Intravascular lithotripsy: A Novel Technology for Treating Calcified Coronary Stenoses Cardiovascular News," Online Available at <https://cardiovascularnews.com/intravascular-lithotripsy-anovel-technology-for-treating-calcified-coronary-stenoses> Apr. 18, 2018, pp. 1-4.
Mooney et al., (1990). "Monorail Piccolino Catheter: A New Rapid Exchange/Ultralow Profile Coronary Angioplasty System," Catheterization and Cardiovascular Diagnosis, 20:114-119.
Mori et al., "Coronary Artery Calcification and its Progression—What Does it Really Mean", American College of Cardiology Foundation, vol. 11, No. 1, 2018, 16 pages.
Myler et al., (1987). "Recurrence After Coronary Aangioplasty," Catheterization and Cardiovascular Diagnosis, 13:77-86.
Nichols et al., (2005). "McDonald's Blood Flow in Arteries: Theoretical," Experimental and Clinical Principles 5th Edition, pp. 1-9.
Nisonson et al., (1986). "Ambulatory Extracorporeal Shockwave Lithotripsy," Urology, 28(5):381-384.
Non Final Office Action received for U.S. Appl. No. 12/482,995, mailed on Aug. 13, 2014, 10 pages.
Non Final Office Action received for U.S. Appl. No. 12/482,995, mailed on Jul. 12, 2013, 11 pages.
Non Final Office Action received for U.S. Appl. No. 12/611,997, mailed on Nov. 26, 2014, 8 pages.
Non Final Office Action received for U.S. Appl. No. 13/207,381, mailed on Nov. 25, 2014, 5 pages.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non Final Office Action received for U.S. Appl. No. 14/079,463, mailed on Mar. 4, 2014, 9 pages.
Non Final Office Action received for U.S. Appl. No. 12/482,995, mailed on Feb. 11, 2011, 27 pages.
Non Final Office Action received for U.S. Appl. No. 12/611,997, mailed on Apr. 8, 2013, 9 pages.
Non Final Office Action received for U.S. Appl. No. 12/611,997, mailed on Aug. 24, 2012, 11 pages.

(56) References Cited

OTHER PUBLICATIONS

Non Final Office Action received for U.S. Appl. No. 12/611,997, mailed on Jun. 21, 2011, 13 pages.
Non Final Office Action received for U.S. Appl. No. 13/049,199, mailed on Dec. 12, 2011, 10 pages.
Non Final Office Action received for U.S. Appl. No. 13/207,381, mailed on Feb. 22, 2013, 7 pages.
Non Final Office Action received for U.S. Appl. No. 13/207,381, mailed on Jun. 12, 2012, 6 pages.
Non Final Office Action received for U.S. Appl. No. 13/534,658, mailed on Mar. 11, 2016, 12 pages.
Non Final Office Action received for U.S. Appl. No. 14/218,858, mailed on Mar. 30, 2016, 13 pages.
Non Final Office Action received for U.S. Appl. No. 14/515,130, mailed on Jan. 14, 2016, 16 pages.
Non-Final Office Action received for U.S. Appl. No. 12/501,619, mailed on Jan. 28, 2014, 10 pages.
Non-Final Office Action received for U.S. Appl. No. 12/581,295, mailed on Jan. 15, 2015, 14 pages.
Non-Final Office Action received for U.S. Appl. No. 12/581,295, mailed on Mar. 10, 2014, 11 pages.
Non-Final Office Action received for U.S. Appl. No. 12/611,997, mailed on Feb. 13, 2014, 9 pages.
Non-Final Office Action received for U.S. Appl. No. 13/049,199, mailed on Feb. 4, 2014, 8 pages.
Non-Final Office Action received for U.S. Appl. No. 13/207,381, mailed on Feb. 25, 2014, 8 pages.
Non-Final Office Action received for U.S. Appl. No. 13/267,383, mailed on Feb. 25, 2015, 9 pages.
Non-Final Office Action received for U.S. Appl. No. 13/465,264, mailed on Dec. 23, 2014, 13 pages.
Non-Final Office Action received for U.S. Appl. No. 13/615,107, mailed on Apr. 24, 2015, 9 pages.
Non-Final Office Action received for U.S. Appl. No. 13/646,583, mailed on Oct. 31, 2014, 8 pages.
Non-Final Office Action received for U.S. Appl. No. 13/962,315, mailed on Aug. 26, 2015, 20 pages.
Non-Final Office Action received for U.S. Appl. No. 14/061,554, mailed on Mar. 12, 2014, 14 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Non-Final Office Action received for U.S. Appl. No. 14/273,063, mailed on Jun. 3, 2016, 9 pages.
Non-Final Office Action received for U.S. Appl. No. 14/660,539, mailed on Nov. 24, 2017, 10 pages.
Non-Final Office Action received for U.S. Appl. No. 14/693,155, mailed on Jan. 15, 2016, 6 pages.
Non-Final Office Action received for U.S. Appl. No. 15/213,105, mailed on Nov. 28, 2017, 7 pages.
Non-Final Office Action received for U.S. Appl. No. 15/346,132, mailed on Dec. 20, 2018, 14 pages.
Non-Final Office Action received for U.S. Appl. No. 15/474,885, mailed on Oct. 5, 2017, 9 pages.
Non-Final Office Action received for U.S. Appl. No. 15/817,073, mailed on Nov. 12, 2019, 18 pages.
Non-Final Office Action received for U.S. Appl. No. 15/979,182, mailed on Aug. 9, 2019, 6 pages.
Non-Final Office Action received for U.S. Appl. No. 16/183,438, mailed on Mar. 31, 2020, 10 pages.
Non-Final Office Action received for U.S. Appl. No. 14/660,539, mailed on Mar. 6, 2017, 14 pages.
Notice of Acceptance Received for Australian Patent Application No. 2009257368, mailed on Aug. 28, 2014, 2 pages.
Notice of Acceptance Received for Australian Patent Application No. 2009313507, mailed on Nov. 17, 2014, 2 pages.
Notice of Acceptance received for Australian Patent Application No. 2013284490, mailed on May 8, 2018, 3 pages.
Notice of Acceptance received for Australian Patent Application No. 2013300176, mailed on Aug. 7, 2017, 3 pages.
Notice of Acceptance received for Australian Patent Application No. 2018204691, mailed on Jun. 18, 2019, 3 pages.
Notice of Allowance received for Canadian Patent Application No. 2,727,429, mailed on May 26, 2015, 1 page.
Notice of Allowance received for Canadian Patent Application No. 2,779,600, mailed on Jul. 7, 2017, 1 page.
Notice of Allowance received for Canadian Patent Application No. 2,881,208, mailed on Oct. 24, 2019, 1 page.
Notice of Allowance received for Chinese Patent Application No. 201380033808.3, mailed on Dec. 29, 2016, 4 pages (Official Copy Only).
Notice of Allowance received for Chinese Patent Application No. 201380041656.1, mailed on Mar. 3, 2017, 4 pages (Official Copy Only).
Notice of Allowance received for Japanese Patent Application No. 2015-036444, mailed on Jan. 13, 2017, 3 pages (Official Copy Only).
Notice of Allowance received for Japanese Patent Application No. 2015-520522, mailed on Feb. 23, 2017, 3 pages (Official Copy Only).
Notice of Allowance received for Japanese Patent Application No. 2015-526523, mailed on Dec. 4, 2017, 3 pages (Official Copy Only) (See Communication under 37 CFR § 1.98(a) (3)).
Notice of Allowance received for Japanese Patent Application No. 2016-143049, mailed on Nov. 13, 2017, 3 pages (Official copy only).
Notice of Allowance received for Japanese Patent Application No. 2017-212658, mailed on May 13, 2019, 3 pages (Official Copy Only).
Notice of Allowance received for U.S. Appl. No. 14/515,130, mailed on May 2, 2016, 8 pages.
Notice of Allowance received for U.S. Appl. No. 14/515,130, mailed on May 25, 2016, 3 pages.
Notice of Allowance received for U.S. Appl. No. 12/581,295, mailed on Jul. 10, 2015, 15 pages.
Notice of Allowance received for U.S. Appl. No. 12/581,295, mailed on Jul. 29, 2015, 7 pages.
Notice of Allowance received for U.S. Appl. No. 12/611,997, mailed on Apr. 15, 2015, 7 pages.
Notice of Allowance received for U.S. Appl. No. 13/207,381, mailed on Apr. 14, 2015, 7 pages.
Notice of Allowance received for U.S. Appl. No. 13/465,264, mailed on May 8, 2015, 7 pages.
Notice of Allowance received for U.S. Appl. No. 13/957,276, mailed on Aug. 28, 2015, 9 pages.
Notice of Allowance received for U.S. Appl. No. 14/271,276, mailed on Feb. 25, 2015, 8 pages.
Notice of Allowance received for U.S. Appl. No. 12/482,995, mailed on Dec. 24, 2014, 6 pages.
Notice of Allowance received for U.S. Appl. No. 13/049,199, mailed on Dec. 15, 2014, 7 pages.
Notice of Allowance received for U.S. Appl. No. 13/049,199, mailed on Jan. 13, 2015, 4 pages.
Notice of Allowance received for U.S. Appl. No. 13/534,658, mailed on Jan. 5, 2017, 6 pages.
Notice of Allowance received for U.S. Appl. No. 13/534,658, mailed on Jan. 18, 2017, 4 pages.
Notice of Allowance received for U.S. Appl. No. 13/646,570, mailed on Mar. 11, 2015, 7 pages.
Notice of Allowance received for U.S. Appl. No. 13/777,807, mailed on May 19, 2015, 13 pages.
Notice of Allowance received for U.S. Appl. No. 13/831,543, mailed on Oct. 8, 2014, 14 pages.
Notice of Allowance received for U.S. Appl. No. 14/061,554, mailed on Apr. 25, 2014, 8 pages.
Notice of Allowance received for U.S. Appl. No. 14/079,463, mailed on Apr. 1, 2014, 5 pages.
Notice of Allowance received for U.S. Appl. No. 14/218,858, mailed on Aug. 26, 2016, 8 pages.
Notice of Allowance received for U.S. Appl. No. 14/271,342, mailed on Mar. 13, 2015, 5 pages.

(56) References Cited

OTHER PUBLICATIONS

Notice of Allowance received for U.S. Appl. No. 14/660,539, mailed on Apr. 6, 2018, 7 pages.
Notice of Allowance received for U.S. Appl. No. 14/693,155, mailed on Apr. 26, 2016, 9 pages.
Notice of Allowance received for U.S. Appl. No. 15/213,105, mailed on Aug. 10, 2018, 8 pages.
Notice of Allowance received for U.S. Appl. No. 15/220,999, mailed on Oct. 10, 2018, 10 pages.
Notice of Allowance received for U.S. Appl. No. 15/346,132, mailed on Aug. 21, 2019, 8 pages.
Notice of Allowance received for U.S. Appl. No. 15/346,132, mailed on Dec. 17, 2019, 7 pages.
Notice of Allowance received for U.S. Appl. No. 15/474,885, mailed on Feb. 14, 2018, 5 pages.
Notice of Allowance received for U.S. Appl. No. 15/817,073, mailed on Mar. 13, 2020, 8 pages.
Notice of Allowance received for U.S. Appl. No. 16/544,516, mailed on May 5, 2020, 7 pages.
Notice of Allowance received for U.S. Appl. No. 13/615,107, mailed on Dec. 31, 2015, 10 pages.
Office Action received for Japanese Patent Application No. 2016-143049, mailed on Jul. 28, 2017, 7 pages (4 pages of English Translation and 3 pages of Official copy).
Office Action received for Australian Patent Application No. 2009257368, issued on Apr. 28, 2014, 4 pages.
Office Action received for Australian Patent Application No. 2009257368, issued on Jul. 31, 2013, 4 pages.
Office Action received for Australian Patent Application No. 2009313507, mailed on Nov. 13, 2013, 3 pages.
Office Action received for Australian Patent Application No. 2013284490, mailed on Jun. 5, 2017, 4 pages.
Office Action received for Australian Patent Application No. 2013284490, mailed on May 3, 2018, 5 pages.
Office Action received for Australian Patent Application No. 2013300176, mailed on Nov. 10, 2016, 2 pages.
Office Action received for Australian Patent Application No. 2018204691, mailed on Jul. 12, 2018, 2 pages.
Office Action received for Canadian Patent Application No. 2,727,429, mailed on Apr. 14, 2015, 4 pages.
Office Action received for Canadian Patent Application No. 2,779,600, mailed on Jan. 4, 2016, 6 pages.
Office Action received for Canadian Patent Application No. 2,877,160, mailed on Feb. 7, 2019, 4 pages.
Office Action received for Canadian Patent Application No. 2,881,208, mailed on Feb. 12, 2019, 4 pages.
Office Action received for Canadian Patent Application No. 2,779,600, mailed on Oct. 19, 2016, 3 pages.
Office Action received for Chinese Patent Application No. 200980153687.X, mailed on Dec. 26, 2012, 11 pages of Official copy only.
Office Action received for Chinese Patent Application No. 200980153687.X, mailed on Jul. 11, 2013, 11 pages (Official copy only).
Office Action received for Chinese Patent Application No. 201380033808.3, mailed on Jul. 5, 2016, 9 pages (3 pages of English translation and 6 pages of Official copy).
Office Action received for Chinese Patent Application No. 201380041656.1, mailed on Jul. 5, 2016, 9 pages (4 pages of English translation and 5 pages of Official copy).
Office Action received for Chinese Patent Application No. 201380042887.4, mailed on Aug. 8, 2016, 9 pages (4 pages of English translation and 5 pages of Official copy).
Office Action received for European Patent Application No. 13735174.8, mailed on Oct. 15, 2018, 5 pages.
Office Action received for European Patent Application No. 09763640.1, mailed on Dec. 2, 2016, 4 pages.
Office Action received for Japanese Patent Application No. 2011-513694, mailed on Aug. 27, 2013, 6 pages (3 pages of English Translation and 3 pages of Official copy).
Office Action Received for Japanese Patent Application No. 2011-513694, mailed on Jun. 10, 2014, 4 pages total (2 pages of Official Copy and 2 pages of English Translation).
Office Action Received for Japanese Patent Application No. 2011-534914, mailed on Jan. 13, 2015, 9 pages(7 pages of English Translation and 2 pages of Official Copy.
Office Action Received for Japanese Patent Application No. 2011-534914, mailed on Jul. 15, 2014, 3 pages (1 page of English Translation and 2 pages of Official Copy).
Office Action received for Japanese Patent Application No. 2011-534914, mailed on May 10, 2016, 10 pages ( 4 pages of Official Copy and 6 pages of English Translation).
Office Action received for Japanese Patent Application No. 2011-534914, mailed on Oct. 1, 2013, 5 pages (2 pages of English Translation and 3 pages of Official copy).
Office Action received for Japanese Patent Application No. 2014-158517, mailed on Feb. 15, 2017, 8 pages (5 pages of English Translation and 3 pages of Official Copy Only).
Office Action Received for Japanese Patent Application No. 2014-158517, mailed on Jun. 22, 2017. 14 pages of official Copy only.
Office Action Received for Japanese Patent Application No. 2014-158517, mailed on May 19, 2015, 5 pages (2 pages of English Translation and 3 pages of Official Copy).
Office Action received for Japanese Patent Application No. 2015-036444, mailed on Feb. 23, 2016, 3 pages of English translation only.
Office Action received for Japanese Patent Application No. 2015-526523, mailed on Jan. 25, 2017, 8 pages (5 pages of English Translation and 3 pages of Official Copy Only).
Office Action received for Japanese Patent Application No. 2016-143049, mailed on Apr. 24, 2017. 5 pages ( 2 pages of English Translation and 3 pages of Official copy).
Office Action received for Japanese Patent Application No. 2017-212658, mailed on Dec. 20, 2018, 10 pages (6 pages of English Translation and 4 pages of Official Copy).
Office Action received for Japanese Patent Application No. 2017-212658, mailed on Sep. 12, 2018, 8 pages (5 pages of English Translation and 3 pages of Official Copy).
Office Action received for Japanese Patent Application No. 2017-212659, mailed on Jul. 5, 2018, 2 pages (Official Copy Only).
Office Action received for Japanese Patent Application No. 2017-212659, mailed on Mar. 4, 2019, 2 pages (Official Copy Only).
Office Action received for Japanese Patent Application No. 2015-036444, mailed on Sep. 14, 2016, 5 pages (3 Pages of English Translation and 2 Pages of Official Copy).
Office Action received for Japanese Patent Application No. 2016-094326, mailed on Dec. 2, 2016, 4 pages (2 pages of English Translation and 2 pages Official Copy Only).
Office Action received for Japanese Patent Application No. 2016-094326, mailed on Jul. 6, 2017, 2 pages (Official Copy Only).
Operator's Manual Intravascular Lithotripsy (IVL) Generator and Connector Cable LBL 61876 Rev. E Mar. 2018, pp. 1-16.
Kini et al., "Optical Coherence Tomography Assessment of the Mechanistic Effects of Rotational and Orbital Atherectomy in Severely Calcified Coronary Lesions," Catheterization and Cardiovascular Interventions, vol. 86, 2015, pp. 1024-1032.
Oral Argument *Cardiovascular Systems Inc.* vs. *Shockwave Medical Inc.* in Inter Partes Review No. IPR2019-00405, dated May 8, 2019, 35 pages.
Otsuka et al., "Has Our Understanding of Calcification in Human Coronary Atherosclerosis Progressed", Coronary Calcification, Apr. 2014, pp. 724-738.
Patent Owner Preliminary Response for U.S. Pat. No. 8,956,371, by the Patent Trial and Appeal Board dated Apr. 10, 2019, 79 pages.
Patent Owner Preliminary Response for U.S. Pat. No. 9,642,673, by the Patent Trial and Appeal Board dated Apr. 24, 2019, 56 pages.
Patent Owner Sur-Reply for U.S. Pat. No. 8,956,371, by the Patent Trial and Appeal Board dated May 24, 2019, 8 pages.
Patent Owner's Response, Nov. 7, 2019, 70 pages.
Patent Owner's Response Case No. IPR2019-00409 Nov. 3, 2019, 65 pages.
Patent Owner's Updated Exhibit List for U.S. Pat. No. 8,956,371, by the Patent Trial and Appeal Board dated May 24, 2019, 7 pages.

(56) References Cited

OTHER PUBLICATIONS

Patent Owner's Sur-Reply for U.S. Pat. No. 8,956,371, by the Patent Trial and Appeal Board dated Mar. 20, 2020, Mar. 20, 2020, 53 pages.
Patent Owner's Updated Exhibit List for U.S. Pat. No. 8,956,371, by the Patent Trial and Appeal Board dated Mar. 20, 2020, 18 pages.
Patterson et al., (1985). "The Etiology and Treatment of delayed Bleeding following Percutaneous Lithotripsy," The Journal of Urology, 133:447-451.
Peripheral Diamondback 360 Peripheral OAS, Micro Crown, Patents, Cardiovascular Systems, Inc., 2017, 6 pages.
Peripheral IVL Case Setup and Execution Shockwave Medical Inc., Available Online at <http://shockwavemedical.com/wp-content/uploads/2018/12/PAD-IVL-Case-Set-Up.pdf>, pp. 1-11.
Petition for Inter Partes Review for U.S. Pat. No. 8,956,371, issued on Feb. 17, 2015, 75 pages.
Petition for Inter Partes Review of U.S. Pat. No. 9,642,673, issued on May 9, 2017, 77 pages.
Petitioner Power of Attorney for U.S. Pat. No. 8,956,371, dated Dec. 6, 2018, pp. 1-2.
Petitioner Power of Attorney for U.S. Pat. No. 9,642,673, dated Dec. 6, 2018, pp. 1-2.
Petitioner's Reply Brief Case IPR2019-00405 Feb. 21, 2020, 65 pages.
Petitioner's Reply Brief, Dated Feb. 18, 2020, 32 pages.
Petitioner's Reply to Patent Owner's Preliminary Response for U.S. Pat. No. 8,956,371, by the Patent Trial and Appeal Board dated May 15, 2019, 7 pages.
Press Release: Shockwave Medical Reports Fourth Quarter and Full Year 2019 Financial Results and Provides Full Year 2020 Financial Outlook, Mar. 4, 2020, 7 pages.
Press Release: St. Francis Participates in Landmark Study Using Sonic Pressure Waves to Treat Heart Blockages, Catholic Health, Jan. 17, 2019, 5 pages.
Publicly Available Professional & Educational Background Summary for Actus Medical, Nov. 2, 2020, 9 pages.
Publicly Available Professional & Educational Background Summary for Alex Asconeguy, Nov. 2, 2020, 4 pages.
Publicly Available Professional & Educational Background Summary for Chris Kunis, 2012, 3 pages.
Publicly Available Professional & Educational Background Summary for Clifton Alferness Exhibit 1229 2013, 3 pages.
Publicly available Professional & Educational Background Summary for Daniel Hawkins Exhibit 1226, 2018, 2 pages.
Publicly Available Professional & Educational Background Summary for Doug Hakala, 2016, 5 pages.
Publicly available Professional & Educational Background Summary for Guy Levy Exhibit 1253 2019, 2 pages.
Publicly Available Professional & Educational Background Summary for J. Christopher Flaherty, Nov. 2, 2020, 2 pages.
Publicly available Professional & Educational Background Summary for John Adams Exhibit 1221, 2009, 2 pages.
Publicly available Professional & Educational Background Summary for Krishna Bhatta Exhibit 1251, 2005, 2 pages.
Publicly available Professional & Educational Background Summary for Marat Izrailevich Lerner, Exhibit 1271, 2020, 3 pages.
Publicly available Professional & Educational Background Summary for Marat Lerner, Exhibit 1272, 2008-2020, 4 pages.
Publicly Available Professional & Educational Background Summary for Michael D. Lesh, 2017, 4 pages.
Publicly available Professional & Educational Background Summary for Naoki Uchiyama 2020, 2 pages.
Publicly available Professional & Educational Background Summary for Ralph de la Torre Exhibit 1252 2010, 2 pages.
Publicly Available Professional & Educational Background Summary for Randy Werneth, Nov. 2, 2020, 3 pages.
Publicly available Professional & Educational Background Summary for Robert Mantell Exhibit 1256 2000, 2 pages.
Publicly available Professional & Educational Background Summary for Stepan Khachin 2008-2020, 3 pages.

Publicly Available Professional & Educational Background Summary for Tom Goff, 2017, 3 pages.
Publicly available Professional & Educational Background Summary for Valery Diamant Exhibit 1257 2017, 2 pages.
Response to Final Office Action received for U.S. Appl. No. 12/482,995, filed Sep. 19, 2011 Sep. 19, 2011, 20 pages.
Ricks (2019). "Long Island Doctors Using Sound Waves to Loosen Calcium Deposits from Arteries, Restore Blood Flow," News/Health, Available Online at <https://www.newsday.com/news/health/calcium-treatment-st-francis-hospital-1.27314331>, pp. 1-4.
Rocha-Singh et al. (2014). "Peripheral Arterial Calcification: Prevalence, Mechanism, Detection, and Clinical Implications," Catheterization and Cardiovascular Interventions, vol. 86, pp. E212-E220.
Rosenschein et al., (1992). "Shock-Wave Thrombus Ablation, a New Method for Noninvasive Mechanical Thrombolysis," The American Journal of Cardiology, 70:1358-1361.
Salunke et al., (2001). "Compressive Stress-Relaxation of Human Atherosclerotic Plaque," J Biomed Mater, 55:236-241.
Sasaki et al., (2015). New Insight into Scar-related Ventricular Tachycardia Circuits in Ischemic Cardiomyopathy: Fat Deposition after Myocardial Infarction on Computed Tomography, Heart Rhythm, 12(7):1508-1518.
Schenkman, Noah Ureter Anatomy WebMD LLC, Emedicine.medscape.com, Jul. 10, 2013, 8 pages.
Second Declaration of Natalie J. Grace dated May 24, 2019, pp. 1-2.
Shlofmitz et al., (2019). "Orbital Atherectomy: A Comprehensive Review," Interv Cardiol Clin, 8(2):161-171.
ShockwaveMedical.com Intravascular Lithotripsy (IVL) Available Online at <https://shockwavemedical.com/technology/intravascular-lithotripsy-ivl/?country=Egypt> 2019, pp. 1-4.
Simpson et al., (1962). "A New Catheter System for Coronary Angioplasty," The American Journal of Cardiology, 49:1216-1222.
Smith et al., (1992). "Microwave Thermal Balloon Angioplasty in the Normal Rabbit," American Heart Journal, 123(6):1516-1521.
Sokol (2011). "Clinical Anatomy of the Uterus, Fallopian Tubes, and Ovaries," Glob. Libr. Women's Med., pp. 1-12.
Soukas, "Deposition Transcript (compressed) of Peter Soukas, Cases:—IPR2019-00405, IPR2019-00408, IPR2019-00409," Dec. 30, 2019, 10 pages.
Stephens, William, "Deposition Transcript (compressed) of William Patrick Stephens," Case No. IPR2019-00408, Jan. 22, 2020, 55 pages.
Supplemental Declaration of Dr. Morten Olgaard Jensen Case IPR2019-00405 Feb. 21, 2020, 136 pages.
Sweers et al. (2012). "Lightning Strikes: Protection, Inspection, and Repair," Aero Magazine, Quarter 4, pp. 19-28.
Tanaka et al., (2001). "A New Radiofrequency Thermal Balloon Catheter for Pulmonary Vein Isolation," Journal of the American College of Cardiology, 38(7):2079-2086.
Thiem et al., (2018). "The 12-Month Results of the EffPac Trial," Journal of Vascular Surgery, 68(55):e122-e123.
Third Party Preissuance Submission for U.S. Appl. No. 15/817,073, filed Aug. 5, 2019, 3 pages.
Third Party Preissuance Submission for U.S. Appl. No. 16/240,556, filed on Sep. 20, 2019, 3 pages.
Third-Party Submission Under 37 CFR 1.290 Concise Description of Relevance for U.S. Appl. No. 15/817,073, filed Aug. 5, 2019, 3 pages.
Third-Party Submission Under 37 CFR 1.290 Concise Description of Relevance for U.S. Appl. No. 16/028,225, filed Aug. 2, 2019, 4 pages.
Third-Party Submission Under 37 CFR 1.290 Concise Description of Relevance for U.S. Appl. No. 16/240,556, filed Sep. 20, 2019, 4 pages.
Tomlinson (1991). "Electrical Networks and Filters: Theory and Design," Prentice Hall, pp. 1-9.
Top Cardiovascular Innovation Award Cardiovascular Research Technologies (CRT) 2015, 1 page.
U.S. Appl. No. 16/993,114, filed Sep. 13, 2020, titled "Low Profile Electrodes for a Shock Wave Catheter,".
Viljoen (2008). "Flashover Performance of a Rod-Rod Gap Containing a Floating Rod Under Switching Impulses with Critical and

(56) References Cited

OTHER PUBLICATIONS

Near Critical Times to Crest," A Dissertation Submitted to the Faculty of Engineering and the Built Environment, University of the Witwatersrand, 128 pages.

Vorreuther et al. (1992). "Impact of Voltage and Capacity on the Electrical and Acoustic Output of Intracorporeal Electrohydraulic Lithotripsy," Urological Research, 20(5):355-359.

Vorreuther et al. (1992). "Publication Information—Impact of Voltage and Capacity on the Electrical and Acoustic Output of Intracorporeal Electrohydraulic Lithotripsy," Urological Research, 20, No. 5, Available Online at <https://rd.springer.com/article/10.1007/BF00922748>): pp. 1-3.

Wagner et al. (1961). "Mechanism of Breakdown of Laboratory Gaps," Transactions of the American Institute of Electrical Engineers. Part III: Power Apparatus and Systems, 80(3):604-618.

Wakerly (1990). "Digital Design: Principles and Practices," Prentice Hall Inc., pp. 1-19.

WebMD.com Definition of 'Angioplasty' Available Online at <https://www.webmd.com/heart-disease/heart-failure/qa/what-is-the-definition-of-angioplasty> Oct. 29, 2017, pp. 1-2.

Weide, Daniel, "Deposition Transcript (compressed) of Daniel Van Der Weide, Ph.d.," Exhibit 1203, Case No. IPR2019-00408, U.S. Pat. No. 9,642,673 B2, Jan. 13, 2020, 94 pages.

Weide, Daniel, "Exhibit 1116 to Deposition of Daniel Van Der Weide," Jan. 13, 2020, 1 page.

Weide, Daniel, "Exhibit to 1117 Deposition of Daniel Van Der Weide, Ph.d.," Jan. 13, 2020, 1 page.

Weide, Daniel, "Exhibit to 1118 Deposition of Daniel Van Der Weide, Ph.d.," Jan. 13, 2020, 1 page.

Wells Fargo Securities LLC, "SWAV: Initiating With A Market Perform Rating," Shockwave Medical Inc., Apr. 1, 2019, pp. 1-34.

Whitaker (2001). "Modelling of Three-Dimensional Field Around Lightning Rods," University of Tasmania, pp. 1-64.

Whitaker (2001). "Publication Information—Modelling of Three-Dimensional Field Around Lightning Rods," University of Tasmania, 1 page.

Written Opinion received for PCT Patent Application No. PCT/US2012/023172, mailed on Sep. 28, 2012, 4 pages.

Written Opinion received for PCT Patent Application No. PCT/US2009/047070, mailed on Jan. 19, 2010, 5 pages.

Yamamoto et al., (2018). "Effect of orbital atherectomy in calcified coronary artery lesions as assessed by optical coherence tomography," Catheter Cardiovasc Interv, 93(7):1211-1218.

Zhong et al., (1997). "Publication Information—Transient Oscillation of Cavitation Bubbles Near Stone Surface During Electrohydraulic Lithotripsy," Journal of Endourology, 11, 1 page.

Zhong et al., (1997). "Transient Oscillation of Cavitation Bubbles Near Stone Surface During Electrohydraulic Lithotripsy," Journal of Endourology, 11(1):55-61.

Peripheral Intravascular Lithotripsy (IVL) Catheter—Instructions for Use (IFU) LBL 61932, Rev A Instructions for Use US Jan. 2018, pp. 1-5.

Peripheral Intravascular Lithotripsy (IVL) Catheter Instructions for Use (IFU) LBL 61959, Rev. B Instructions for Use Jun. 2018, pp. 1-7.

After Orbital Atherectomy Video (post treatment) Video 2019.

Before Orbital Aterectomy Video (pre-treatment) Video 2019.

Dictionary.com, (2019). "Definition of 'Angioplasty'," Available Online at <https://www.dictionary.com/browse/angioplasty>, 5 pages.

Goryachev et al., (1997). "Mechanism of Electrode Erosion in Pulsed Discharges in Water with a Pulse Energy of ~1 J," Tech. Phys. Lett. vol. 23(5):386-387.

Med Device Online, (retrieved on Aug. 4, 2020). "Angioplasty Balloons Advanced Polymers Inc.," Available Online at <https://www.meddeviceonline.com/doc/angioplasty-balloons-0001>, 1 page.

MedlinePlus, (2018). "Angioplasty U.S. National Library of Medicine," Available Online at <https://medlineplus.gov/angioplasty.html>, 4 pages.

Extended European Search Report and Search Opinion received for European Patent Application No. 23208960.7, mailed on Feb. 5, 2024, 6 pages.

Office Action received for Chinese Patent Application No. 202080081289.8, mailed on Jul. 9, 2024, 16 pages (7 pages of English translation and 9 pages of Official copy).

Notice of Allowance received for U.S. Appl. No. 18/114,882, mailed on Nov. 14, 2024, 8 pages.

Non-Final Office Action received for U.S. Appl. No. 18/114,882, mailed on Sep. 5, 2024, 12 pages.

Non-Final Office Action received for U.S. Appl. No. 16/993,114, mailed on Feb. 6, 2025, 22 pages.

Notice of Allowance received for European Patent Application No. 23208960.7, mailed on Oct. 2, 2024, 7 pages.

Extended European Search Report and Search Opinion received for European Patent Application No. 25150787.7, mailed on Apr. 7, 2025, 10 pages.

Office Action received for Australian Patent Application No. 2020354885, mailed on Mar. 17, 2025, 3 pages.

Office Action received for Chinese Patent Application No. 202080081289.8, mailed on Mar. 17, 2025, 17 pages. English Translation.

Notice of Allowance received for Japanese Patent Application No. 2022-518250, mailed on Sep. 25, 2024, 5 pages. English translation.

Office Action received for Japanese Patent Application No. 2022-518250, mailed on Mar. 19, 2024, 20 pages. English translation.

\* cited by examiner

LOW PROFILE ELECTRODES FOR A SHOCK WAVE CATHETER

CROSS-REFERENCE TO RELATED APPLICATIONS

The application claims priority to U.S. Provisional Patent Application No. 62/904,839, entitled "LOW PROFILE ELECTRODES FOR A SHOCK WAVE CATHETER," filed on Sep. 24, 2019, the content of which is hereby incorporated by reference in its entirety.

FIELD OF THE DISCLOSURE

The present disclosure relates generally to shock wave electrodes, and more specifically, to electrodes for the generation of shock waves within vascular structures.

BACKGROUND

The present invention relates to a treatment system for percutaneous coronary angioplasty or peripheral angioplasty in which an angioplasty balloon is used to dilate a lesion (e.g., calcified lesion) and restore normal blood flow in the artery. In this type of procedure, a catheter carrying a balloon is advanced into the vasculature along a guide wire until the balloon is aligned with calcified plaques. The balloon is then pressurized to reduce or break the calcified plaques and push them back into the vessel wall.

More recently, the assignee herein has developed a treatment system that includes electrodes within an angioplasty type balloon. In use, the balloon is advanced to the region of an occlusion. The balloon is then initially pressurized with a conductive fluid. A series of high voltage pulses are applied to the electrodes within the balloon, with each pulse generating a shock wave in the conductive fluid. The shock waves pass through the balloon wall and into the occlusion, cracking the calcified plaques. Once the calcified plaques are cracked, the balloon can be further expanded to open the vessel. Such system is disclosed in U.S. Pat. Nos. 8,956,371, 8,888,788, and U.S. Pub. No. 2019/0150960, all of which are incorporated herein by reference. Further, the assignee herein has developed techniques for providing an electrode on the tip of a guide wire for generating forward directed shock waves. This approach is disclosed in U.S. Patent Publication No. 2015/0320432, also incorporated herein by reference.

The present invention relates techniques for treating tight, hard-to-cross calcific lesions by positioning low-profile shock wave electrodes at the distal portion of the balloon, including the distal leg segment and/or the distal cone segment of the angioplasty balloon.

BRIEF SUMMARY

The invention provides a device for generating shock waves. An exemplary device for generating shock waves comprises an elongated tube; a balloon wrapped circumferentially around a portion of the elongated tube, the balloon comprising: a distal end sealed to the elongated tube, a leg segment proximal to the distal end of the balloon, a cone segment proximal to the leg segment of the balloon, and a straight segment proximal to the cone segment of the balloon, wherein, when the balloon is inflated: the leg segment is substantially cylindrical or is of a tapered shape with an average diameter, the cone segment is of a tapered shape with an average diameter greater than the average diameter of the leg segment, and the straight segment is of a substantially cylindrical shape with a diameter greater than the average diameter of the cone segment; and at least one distal emitter configured to generate shock waves, wherein the at least one distal emitter is positioned in the leg segment or the cone segment of the balloon.

In some embodiments, at least one distal emitter is positioned in the leg segment of the balloon.

In some embodiments, at least one distal emitter is positioned in the cone segment of the balloon.

In some embodiment, the at least one distal emitter comprises a first distal emitter positioned in the leg segment of the balloon and a second distal emitter positioned in the cone segment of the balloon.

In some embodiments, the at least one distal emitter is located between approximately 0.5 mm and approximately 1 mm from a distal end of a gap between the leg segment of the balloon and the elongated tube.

In some embodiments, when the balloon is inflated, a gap between an inner diameter of the leg segment and an outer diameter of the elongated tube is between around 0.001" to around 0.003".

In some embodiments, the leg segment is less than approximately 3.5 mm long, and the cone segment is approximately 4.5 mm to approximately 5.5 mm long.

In some embodiments, when the balloon is inflated, a first vertex angle between the leg segment of the balloon and the elongated tube is smaller than 5 degrees.

In some embodiments, when the balloon is inflated, a second vertex angle between the cone segment of the balloon and the elongated tube is larger than the first vertex angle.

In some embodiments, the at least one distal emitter comprises a first electrode pair, the first electrode pair comprising: a conductive portion of a first insulated wire and a conductive portion of a second insulated wire.

In some embodiments, the conductive portion of the first insulated wire is formed by removing a first portion of insulation from the first insulated wire, and the conductive portion of the second insulated wire is formed by removing a second portion of insulation from the second insulated wire.

In some embodiments, the first insulated wire comprises a flattened distal segment, and the first portion of insulation is removed from the flattened distal segment of the first insulated wire, and the second insulated wire comprises a flattened distal segment, and the second portion of insulation is removed from the flattened distal segment of the second insulated wire.

In some embodiments, a diameter of the flattened distal segment of the first insulated wire is approximately 47% to 75% of a diameter of a proximal segment of the first insulated wire, and a diameter of the flattened distal segment of the second insulated wire is approximately 47% to 75% of a diameter of a proximal segment of the second insulated wire.

In some embodiments, a layer of polymer covers at least a portion of the first insulated wire and the second insulated wire, such that the conductive portion of the first insulated wire is held a controlled distance apart from the conductive portion of the second insulated wire.

In some embodiments, the at least one distal emitter further comprises a second electrode pair, the second electrode pair comprising: a further conductive portion of the second insulated wire and a conductive portion of a third insulated wire.

In some embodiments, the at least one distal emitter further comprises a second electrode pair and a third electrode pair, wherein the second electrode pair comprises: a further conductive portion of the second insulated wire and a first side edge of a conductive sheath wrapped circumferentially around the elongated tube; and wherein the third electrode pair comprises: a second side edge of the conductive sheath and a conductive portion of a third insulated wire.

In some embodiments, the at least one distal emitter comprises a first electrode pair and a second electrode pair, wherein the first electrode pair comprises: a conductive portion of a first insulated wire and a first side edge of a conductive sheath wrapped circumferentially around the elongated tube; and wherein the second electrode pair comprises: a second side edge of the conductive sheath and a conductive portion of a second insulated wire.

In some embodiments, the first side edge and the second side edge are positioned circumferentially 180 degrees on opposite edges of the conductive sheath.

In some embodiments, the elongated tube is tapered toward the distal end.

In some embodiments, the device comprises at least one proximal emitter configured to generate shock waves, wherein the at least one proximal emitter is positioned in the straight segment of the balloon.

In some embodiments, the device comprises a variable high voltage pulse generator selectively connected to the at least one distal emitter and the at least one proximal emitter, wherein the variable high voltage pulse generator can be activated to generate shock waves at either the at least one distal emitter or the at least one proximal emitter.

An exemplary method of generating shock waves comprises introducing a shock wave device into a patient's vasculature, the shock wave device comprising: a balloon comprising: a distal end, a leg segment proximal to the distal end of the balloon, a cone segment proximal to the leg segment of the balloon, and a straight segment proximal to the cone segment of the balloon; at least one distal emitter in the leg segment or the cone segment of the balloon; and at least one proximal emitter in the straight segment of the balloon. During a first stage, the method includes advancing the shock wave device in the patient's vasculature such that the distal leg segment of the balloon is advanced as far into the calcified lesion as possible; inflating the balloon with a conductive fluid such that the inflated balloon is gently fixed to walls of the vasculature in direct proximity with the calcified lesion, wherein, when the balloon is inflated, the leg segment is substantially cylindrical or is of a tapered shape with an average diameter, the cone segment is of a tapered shape with an average diameter greater than the average diameter of the leg segment, and the straight segment is of a substantially cylindrical shape with a diameter greater than the average diameter of the cone segment; activating a voltage source to generate shock waves at the at least one distal emitter; and after activating the voltage source, deflating the balloon. During a second stage, the method includes further advancing the shock wave device in the patient's vasculature such that the straight segment of the balloon is advanced as far into the calcified lesion as possible; inflating the balloon with the conductive fluid such that the inflated balloon is gently fixed to walls of the vasculature in direct proximity with the calcified lesion; and activating the voltage source to generate shock waves at the at least one proximal emitter.

In some embodiments, the first stage is repeated until the calcified lesion is modified such that the straight segment of the balloon is able to advance into the calcified lesion.

In some embodiments, activating the voltage source during the second stage generates shock waves at both the at least one proximal emitter and the at least one distal emitter.

In some embodiments, the at least one distal emitter is positioned in the leg segment of the balloon In some embodiments, the at least one distal emitter is positioned in the cone segment of the balloon.

In some embodiments, the at least one distal emitter comprises a first distal emitter positioned in the leg segment of the balloon and a second distal emitter positioned in the cone segment of the balloon.

The invention also provides a device for generating shock waves. An exemplary device for generating shock waves comprises a balloon comprising: a distal end, a leg segment proximal to the distal end of the balloon, a cone segment proximal to the leg segment of the balloon, wherein, when the balloon is inflated: the leg segment is cylindrical or is of a tapered shape with a first vertex angle, and the cone segment is of a tapered shape with a second vertex angle larger than the first vertex angle, an elongated tube extending through the balloon, wherein the balloon wraps around a longitudinal segment of the elongated tube, wherein the distal end of the balloon is sealed to the elongated tube; an electrode pair between the elongated tube and the leg segment of the balloon, comprising: a conductive portion of a first insulated wire extending over the elongated tube, a conductive portion of a second insulated wire extending over the elongated tube, wherein, when a voltage is applied across the first insulated wire and the second insulated wire, a current is configured to flow from the first insulated wire to the second insulated wire, and wherein a shock wave is created across the conductive portion of the first insulated wire and the conductive portion of the second insulated wire.

In some embodiments, the electrode pair is a first electrode pair, and wherein the device comprises a second electrode pair within the cone segment of the balloon.

In some embodiments, the second electrode pair comprises: a conductive portion of the second insulated wire extending over the elongated tube; and a conductive portion of a third insulated wire extending over the elongated tube.

In some embodiments, the second electrode pair comprises: a conductive portion of the second insulated wire extending over the elongated tube; and a conductive sheath circumferentially mounted around the elongated tube.

In some embodiments, the balloon further comprises a straight segment proximal to the cone segment; the devices further comprises a third electrode pair between the elongated tube and the straight segment of the balloon.

In some embodiments, the first electrode pair and the second electrode pair are configured to be driven by a first voltage source, and the third electrode pair is configured to be driven by a second voltage source different from the first voltage source.

In some embodiments, the conductive portion of the first insulated wire is formed by removing a first portion of insulation from the first insulated wire, and wherein the conductive portion of the second insulated wire is formed by removing a second portion of insulation from the second insulated wire.

In some embodiments, the first insulated wire comprises a flattened distal segment, and the first portion of insulation is removed from the flattened distal segment of the first wire, and the second insulated wire comprises a flattened distal segment, and the second portion of insulation is removed from the flattened distal segment of the second wire.

In some embodiments, the distal segment of the first insulated wire and the distal segment of the second insulated wire are secured to the elongated tube via wrapping material.

In some embodiments, the first vertex angle is smaller than 5 degrees.

In some embodiments, wherein the second vertex angle is larger than 5 degrees.

In some embodiments, the elongated tube comprises longitudinal grooves that are spaced apart by 90 degrees, and wherein a first portion of the first wire is placed in a first longitudinal groove and a second portion of the first wire is placed in a second longitudinal groove that is 90 degree from the first groove.

An exemplary method of generating shock waves comprises introducing a shock wave device into a patient's vasculature, the shock wave device comprising: a balloon comprising: a distal end, a leg segment proximal to the distal end of the balloon, a cone segment proximal to the leg segment of the balloon, and a straight segment proximal to the cone segment of the balloon; a first plurality of electrode pairs in the leg segment or the cone segment of the balloon; and a second plurality of electrode pairs in the straight segment of the balloon; advancing the shock wave device within the vasculature such that the leg segment of the balloon is at a treatment site; inflating the balloon with a conductive fluid, wherein, when the balloon is inflated, the leg segment is cylindrical or is of a tapered shape with a first vertex angle, the cone segment is of a tapered shape with a second vertex angle larger than the first vertex angle, the straight segment is of a cylindrical shape; and activating a first voltage source, wherein the first voltage source is configured to generate shock waves at the first set of electrode pairs but not the second set of electrode pairs.

In some embodiments, the method further comprises: after activating the first voltage source, deflating the balloon; advancing the shock wave device; inflating the balloon with a conductive fluid; activating a first voltage source and a second voltage source simultaneously, wherein the second voltage source is configured to generate shock waves at the second set of electrode pairs.

In some embodiments, the method further comprises: after activating the first voltage source, deflating the balloon; advancing the shock wave device; inflating the balloon with a conductive fluid; activating a second voltage source, wherein the second voltage source is configured to generate shock waves at the second set of electrode pairs.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Figure 4:
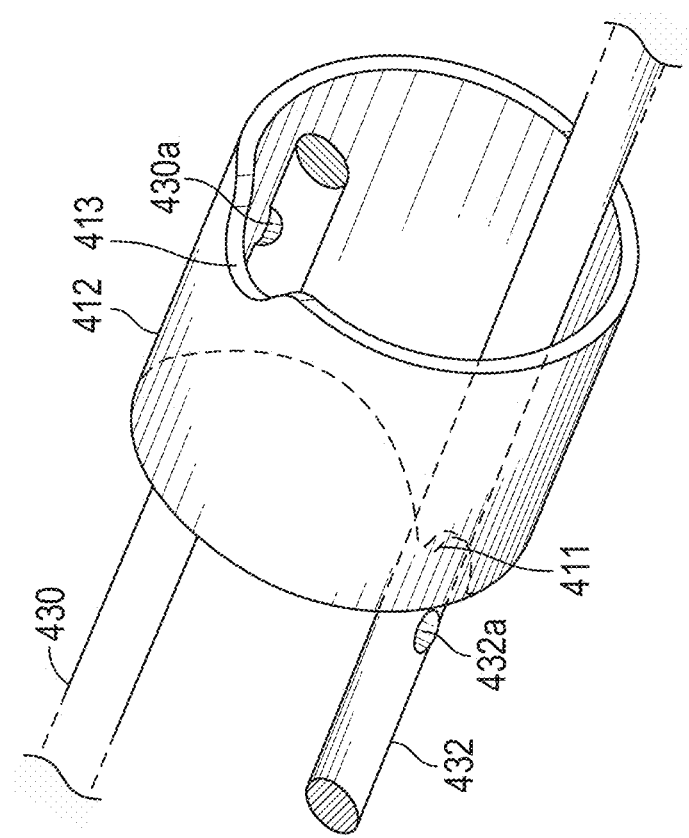
FIG. 4 depicts an exemplary shock wave electrode assembly comprising a conductive sheath and two wires, in accordance with some embodiments.

The assignee herein has developed a number of low-profile shock wave electrodes that may be suitable for use in angioplasty and/or valvuloplasty procedures. For example, in U.S. Pub. No. 2019/0150960, the assignee discloses a low-profile electrode assembly, in which an outer electrode is formed by a conductive sheath, and an inner electrode is formed by removing a portion of an insulated wire (e.g., cutting a hole in the insulating layer near the end of the wire) to expose an electrically conductive portion of the insulated wire. The inner electrode is placed a controlled distance apart from the side edge of the conductive sheath (e.g., as shown in FIG. 4) to allow for a reproducible arc for a given current and voltage.

Figure 1A:
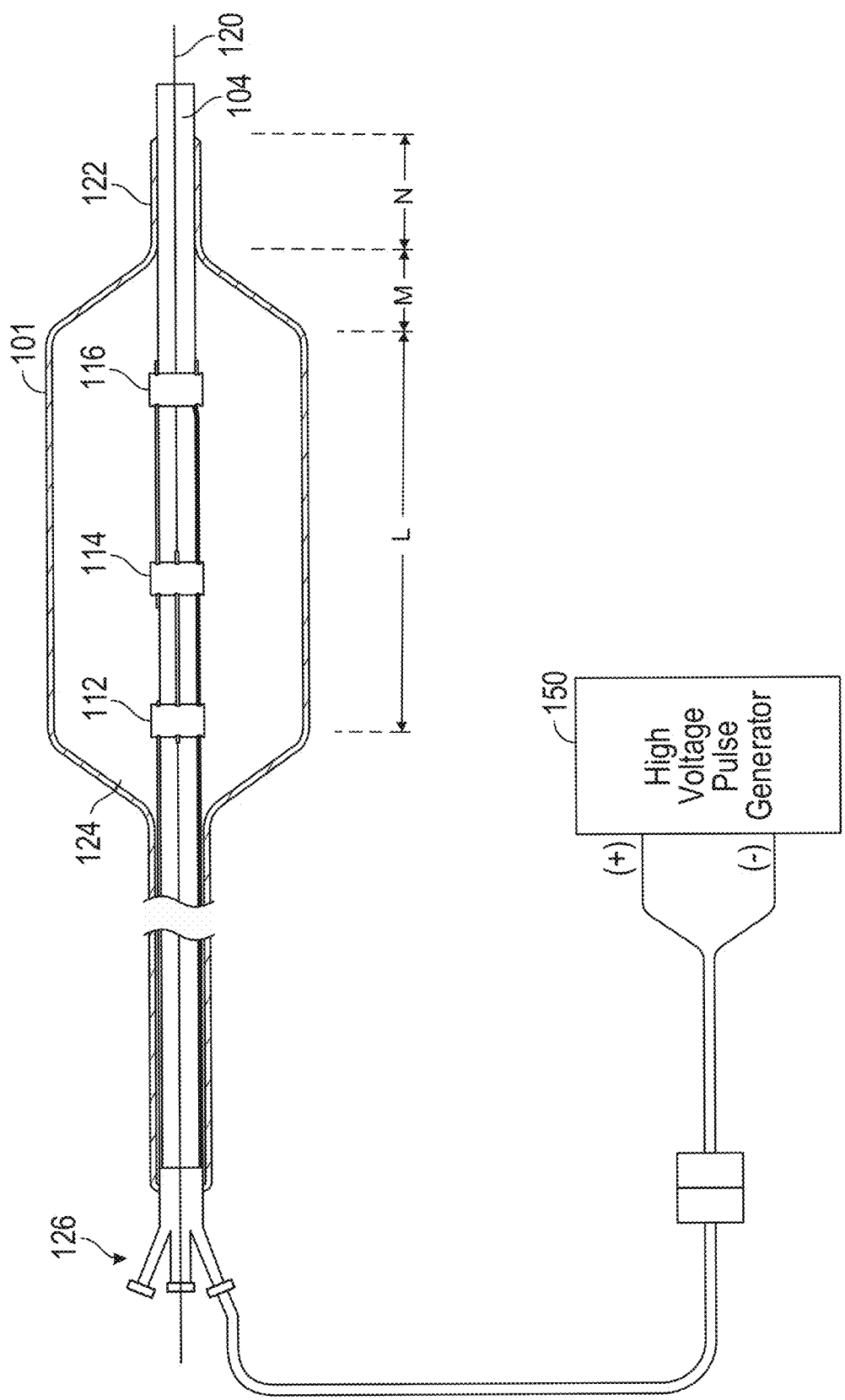
FIG. 1A depicts a prior art shock wave angioplasty device having a plurality of electrode assemblies.

FIG. 1A depicts a prior art shock wave angioplasty device according to assignee's prior filing U.S. Pub. No. 2019/0150960. The shock wave device includes an elongated tube 104 and an angioplasty balloon 101. The angioplasty balloon wraps circumferentially around a portion of the elongated tube 104 in a sealed configuration via, for example, a seal 122. The angioplasty balloon 101 forms an annular channel 124 around the elongated tube 104 through which a conductive fluid, such as saline, may be admitted into the balloon via fill ports 126. The balloon is filled with the fluid such that the balloon can be inflated and gently fixed to the walls of the artery in direct proximity with a calcified lesion. In some embodiments, the fluid may also contain an x-ray contrast to permit fluoroscopic viewing of the catheter during use.

The elongated tube 104 includes a number of longitudinal grooves or channels configured for retaining wires and/or inner electrodes. A plurality of insulated wires are placed within the grooves of the elongated tube 104. Furthermore, a number of conductive sheaths 112, 114, and 116 are circumferentially mounted around the elongated tube 104. A variable high voltage pulse generator 150 is connected to two of the insulated wires. The insulated wires and the sheaths form three electrode assemblies that can be activated to generate shock waves at 6 locations (e.g., along the length of the vessel), as discussed in U.S. Pub. No. 2019/0150960.

The prior art system in FIG. 1A can have a lower crossing profile than contemporary intravascular lithotripsy ("IVL") catheters. However, when the prior art system is used to treat tighter calcified lesions (e.g., having a crossing area smaller than the crossing profile of the prior art system), the prior art system still has drawbacks. As depicted in FIG. 1A, the sheaths 112, 114, and 116 are positioned within the straight segment (labelled "L" in FIG. 1A) of the angioplasty balloon 101, thus generating shock waves only within the straight segment of the balloon. As a result, during treatment, a physician has to advance the balloon catheter until the straight segment (labelled "L") is positioned within the treatment site prior to delivering shock waves. If the calcified lesion is difficult to cross for the prior art system given the cross profile of the straight segment of the balloon (which can be larger than the cross profile of the cone segment and the leg segment due to the size of the conductive sheath and/or the amount of balloon material), additional pre-dilatation and/or pre-treatment devices are needed to ensure optimal positioning of the balloon. The use of a pre-dilatation and/or pre-treatment device adds cost and complexity to the procedure.

Described herein are IVL catheters with one or more miniaturized lithotripsy emitters positioned at the distal segment of the angioplasty balloon (i.e., the distal leg segment "N" and/or distal cone segment "M" of the balloon). Positioning the emitters at the distal portion of the balloon allows IVL treatment in tighter, hard-to-cross calcific lesions and facilitates further crossing of the IVL balloons. The present invention is similar to the prior art system in FIG. 1A in that it can comprise an array of lithotripsy emitters within the straight section of the balloon (labelled "L" in FIG. 1A) to deliver shock waves. In addition, the present invention can further comprise low-profile emitters inside the cone segment (labelled "M") and distal leg segment (labelled "N") to facilitate IVL treatment in tight, hard-to-cross calcific lesions.

Figure 1B:
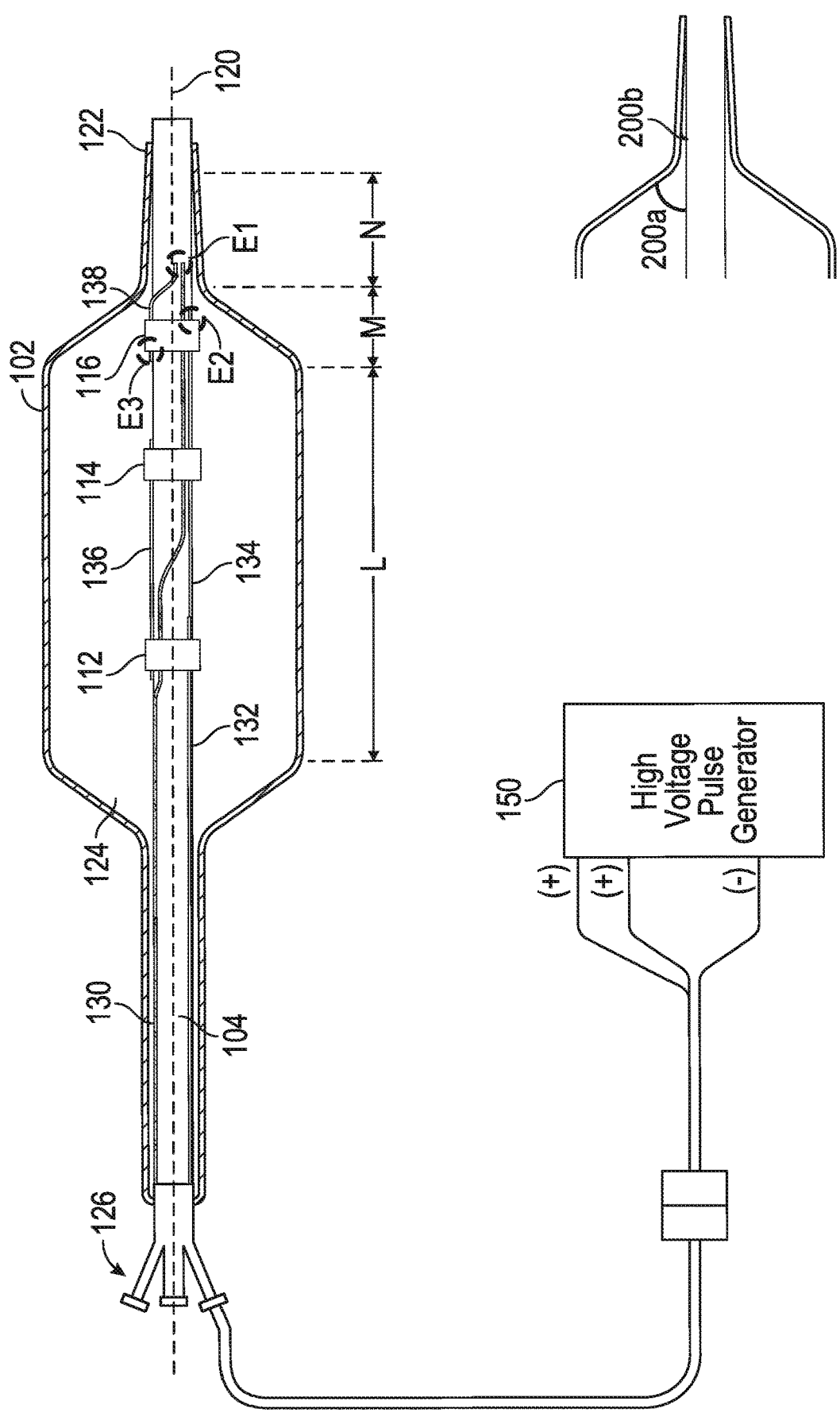
FIG. 1B depicts an exemplary shock wave angioplasty device having a plurality of electrode assemblies, in accordance with some embodiments.

FIG. 1B depicts an exemplary shock wave angioplasty device 100 according to an embodiment of the invention. The shock wave device 100 includes an elongated tube 104 and an angioplasty balloon 102. The angioplasty balloon wraps circumferentially around a portion of the elongated tube 104 in a sealed configuration via, for example, a seal 122. The angioplasty balloon 102 forms an annular channel 124 around the elongated tube 104 through which a conductive fluid, such as saline, may be admitted into the balloon via fill ports 126. The balloon is filled with the fluid such that the balloon can be inflated and gently fixed to the walls of the artery in direct proximity with a calcified lesion. In some embodiments, the fluid may also contain an x-ray contrast to permit fluoroscopic viewing of the catheter during use.

FIG. 1B depicts the angioplasty balloon 102 in an inflated state. As depicted, the balloon includes three longitudinal segments at the distal end: a straight segment (labelled "L"), a cone segment (labelled "M"), and a leg segment (labelled "N"). When inflated, the straight segment is configured to expand into a cylindrical shape or substantially cylindrical shape; the cone segment is configured to expand into a cone or tapered shape; the leg segment is configured to provide no or little expansion. Each of the longitudinal segments has a diameter, which is equal to the distance between a point on the surface of the segment to a corresponding point 180 degrees circumferentially across the balloon. Each of the segments additionally has an average diameter, which is approximated as the sum of the maximum diameter of the segment and the minimum diameter of the segment divided by two. As depicted in FIG. 1B, when inflated, the cone segment has an average diameter that is greater than the average diameter of the leg segment. The straight segment has a diameter greater than the average diameter of the cone segment. As shown in FIG. 1B, when the balloon is inflated, the leg segment is of a cone shape. The vertex angle of the cone segment (200a) is larger than the vertex angle of the leg segment (200b). In some embodiments, the vertex angle 200a is between 5-10° and the vertex angle 200b is between 0-5°. In some embodiments, the vertex angle 200a is between 5-20° and the vertex angle 200b is between 0-5°. In some embodiments, when the balloon is inflated, the leg segment is of a cylindrical shape (i.e., 200b is 0 degree).

By design, there is a gap between the inner diameter of the leg segment of the balloon and the outer diameter of the elongated tube 104 to accommodate a distal emitter (labelled "E1") formed by the distal portions of two wires. Thus, when the balloon is inflated with fluid, the gap is filled with the fluid to allow generation of shock waves at the distal emitter (labelled "E1"). In some embodiments, the gap is between around 0.001"-0.003". In general, the bigger gap (thus more fluid) between the emitter and the balloon wall, the less likely pulsing can negatively impact the balloon integrity. In some embodiments, E1 can be located at ~0.5-1 mm of the distal end of the gap. In some embodiments, the leg segment is approximately 3.5-5.0 mm long, and the cone segment is approximately 4.5-5.5 mm long.

Based on design, the leg segment in some embodiments provides no or little expansion when the balloon is inflated. In a deflated state, the leg segment can be of cylindrical, substantially cylindrical, or slightly tapered (vertex angle smaller than 5 degrees). In an inflated state, the leg segment can be of cylindrical, substantially cylindrical, or slightly tapered (vertex angle smaller than 5 degrees).

The elongated tube 104 includes a number of longitudinal grooves or channels configured for retaining wires and/or inner electrodes. The elongated tube 104 also includes a lumen through which a guide wire 120 is inserted. In the depicted example in FIG. 1B, insulated wires 130, 132, 134, 136, and 138 are placed along the elongated tube 104 (e.g., within the grooves of the elongated tube 104). Furthermore, a number of conductive sheaths 112, 114, and 116 are circumferentially mounted around the elongated tube 104. A variable high voltage pulse generator 150 can provide a first voltage channel between wire 130 and 134 and a second voltage channel between 130 and 132. The insulated wires and the sheaths form seven electrode pairs that can be activated to generate shock waves at 7 locations (e.g., along the length of the vessel) simultaneously or in multiple stages of the IVL treatment, as discussed in detail below.

As shown in FIG. 1B, the second most distal emitter (labelled "E2") and the third most distal emitter (labelled "E3") are placed in the cone segment of the balloon. In the depicted example, E2 is formed by the distal side edge of the sheath 116 and a distal portion of the wire 134. In other embodiments (e.g., FIG. 2A), E2 can be formed by the distal portions of two wires similar to E1.

Accordingly, the exemplary shock wave angioplasty device 100 can generate shock waves in the distal segments ("M" and "N") in addition to the straight segment ("L") of the angioplasty balloon. This is advantageous because the distal segments have a lower profile than the straight segment when the balloon is deflated (e.g., due to the lower amount of surrounding balloon material in the distal segments, due to the use of low-profile wire-to-wire emitters in the distal segments, due to the tapering design of the cone and the leg) and when the balloon is inflated. This can facilitate IVL treatment in tight, hard-to-cross calcific lesions.

In operation, a physician advances the guide wire 120 from an entry site on a patient (e.g., an artery in the groin area of the leg) to the target region of a vessel (e.g., a region having calcified plaques that need to be broken up). The shock wave device shown in FIG. 1B, which comprises the elongated tube 104 with a guide wire lumen and the angioplasty balloon may be advanced over the guide wire to the target region of the vessel. The balloon may be collapsed over the elongated member while the device is advanced through the vasculature. The location of the shock wave device may be determined by x-ray imaging and/or fluoroscopy.

The balloon distal leg segment and cone segment are advanced as far as possible inside the tight lesion. A guide catheter is positioned such that its distal tip is proximal to sheath 116 to retain the deflated state of the straight portion of the balloon. The balloon is then inflated by a conductive fluid (e.g., saline and/or saline mixed with an image contrast agent) to IVL pressure, allowing conductive fluid to fill the leg segment and cone segment of the balloon. In the first stage of the IVL treatment, a voltage is applied between wires 130 and 134 to activate the three most distal emitters E1, E2, and E3 (e.g., for 1 cycle). After the completion of the $1^{st}$ cycle, the balloon is deflated and the balloon distal leg and cone segments are advanced further into the lesion. The balloon is again inflated and another cycle of therapy is applied. Further advancement of the balloon is attempted after the completion of the cycle. In some embodiments, the other emitters are not activated during the first stage of the treatment. In some embodiments, the straight portion of the balloon is retained by a guide catheter until the straight portion of the balloon is able to advance and cross the lesion. After calcium in the tight lesion has been modified and the straight portion of the balloon is able to cross the lesion, the balloon is again inflated to IVL pressure.

In the second stage of the IVL treatment, all of the emitters are activated simultaneously by applying a first voltage across wire 130 and 134 and a second voltage across 130 and 132. In some embodiments, the 3 distal emitters (i.e., E1, E2, and E3) may not be activated if the straight portion of the balloon is able to cross the entire lesion. For example, the physician may simultaneously connect the insulated wire 134 to a first positive lead of the pulse generator, connect the insulated wire 132 to a second positive lead of the pulse generator, and connect the insulated wire 130 to a negative lead or the ground. Alternatively, the physician may only connect the insulated wire 132 to a positive lead of the pulse generator and connect the insulated wire 130 to the negative lead or ground. Shock waves generated by the proximal emitters (i.e., the emitters proximal to the three distal emitters) provide additional treatment to the calcific lesion, while shock waves generated by the three distal emitters E1-E3 allows further advancement of the balloon. The magnitude of the shock waves can be controlled by controlling the magnitude of the pulsed voltage, the current, the duration, and the repetition rate. The physician may start with low energy shock waves and increase the energy as needed to crack the calcified plaques. Such shock waves will be conducted through the fluid, through the balloon, through the blood and vessel wall to the calcified lesion where the energy will break the hardened plaque. The progress of the plaque break-up may be monitored by x-ray and/or fluoroscopy. Once the calcified lesion has been sufficiently treated, the balloon may be inflated further, then deflated, and the shock wave device and guide wire may be withdrawn from the patient.

As such, embodiments of the present invention amount to a crossing and IVL combination catheter. Emitters in the distal balloon leg and cone segments are used to facilitate crossing of the balloon catheter in tight, hard-to-cross lesions. Emitters within the straight segment deliver IVL treatment and dilatation to calcified lesions. In some embodiments, the angioplasty balloon is made of soft grade polymer extrusion (e.g., certain Pebax material) allowing the distal cone and leg segments to withstand higher heat and pressure from IVL treatment.

Figure 1C:
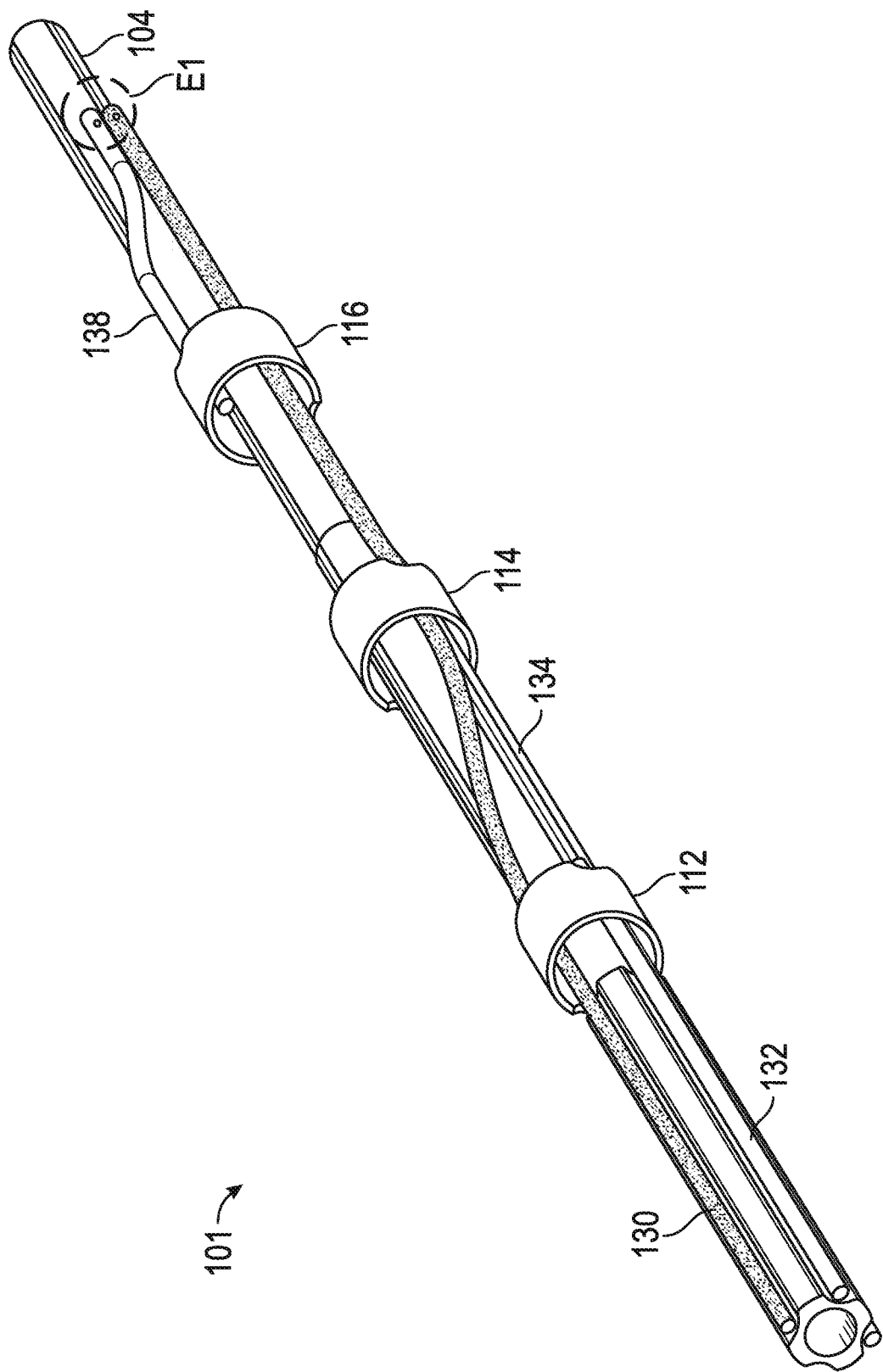
FIG. 1C depicts a set of shock wave electrode assemblies in an exemplary shock wave angioplasty device that may be activated to generate shock waves at multiple locations, in accordance with some embodiments.

FIG. 1C depicts exemplary shock wave electrode assemblies included in the exemplary shock wave angioplasty device 100 of FIG. 1B, according to some embodiments of the invention. The elongated tube 104 provides four longitudinal grooves, as indicated by the proximal end of the elongated tube. In some embodiments, the elongated tube 104 is tapered toward its distal end. A number of insulated wires (e.g., lead or interstation wires) 130, 132, 134, and 136 are disposed on the outer surface of the elongated tube 104 such that they extend along the length of the elongated tube. The wires can be straight or twisted. For example, wire 132 is disposed within one groove of the elongated tube 104, while wire 130 is twisted and different segments of the wire 130 are disposed along different grooves or outer surface of the elongated tube 104.

Figure 1D:
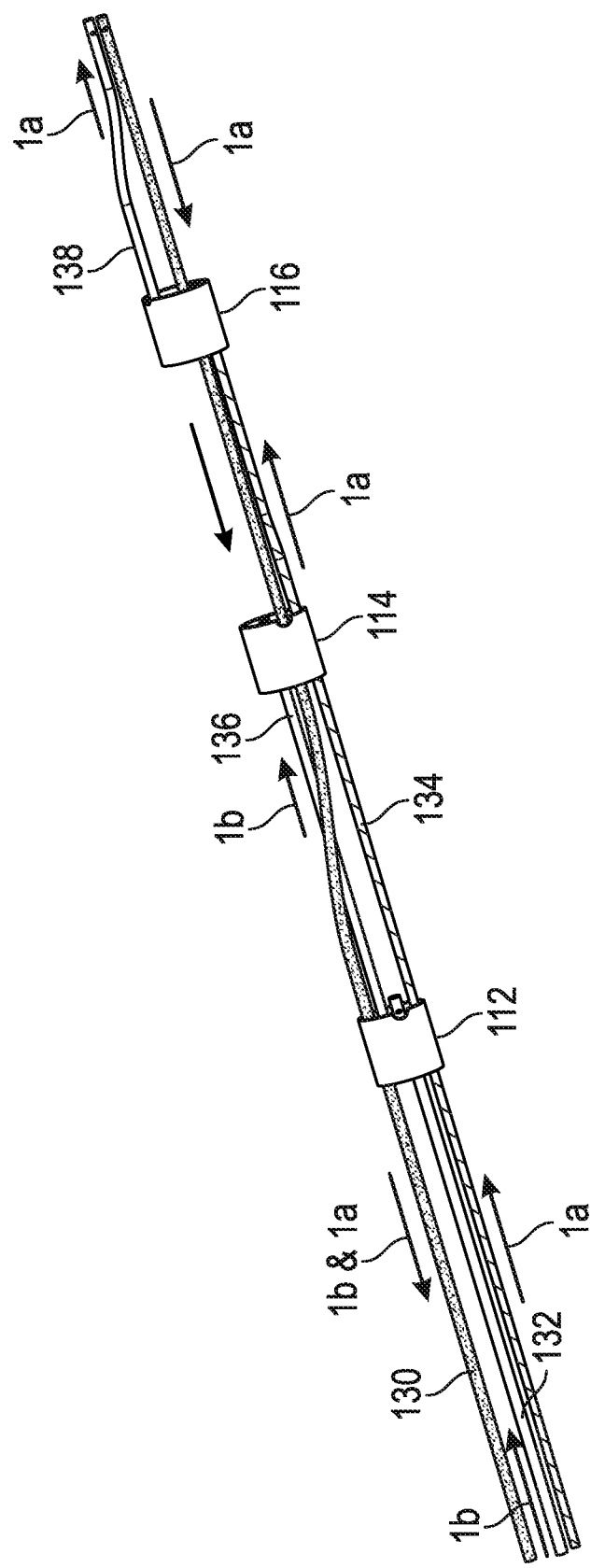
FIG. 1D depicts the connectivity between a plurality of inner electrodes and sheaths to attain the configuration of FIG. 1B, in accordance with some embodiments.

The shock wave angioplasty device 100 further includes three conductive sheaths 112, 114, and 116 each circumferentially mounted around the elongated tube 104. FIG. 1D depicts the relative placement of the wires and the conductive sheaths, with the elongated tube removed. FIG. 1D further depicts two current flows 1a and 1b for generating seven sources of shock waves, as described with reference to FIGS. 1E and 1F.

An emitter can be formed by a side edge of a conductive sheath and a portion of a wire, as described in assignee's prior filing U.S. Pub. No. 2019/0150960. For example, as shown in FIG. 4, a portion of the insulating layer of the wire 430 is removed near the distal end of the wire 430 to expose an electrically conductive wire portion, forming the first inner electrode 430a. In the depicted example, a hole in the insulating layer is cut on the curved outer surface along the length of the wire. The removed portion may be in any shape, such as a circle, a rectangle, a strip around the circumference of the wire, etc. The location, shape, and size of the removed portion may vary to control the location, direction, and/or magnitude of the shock wave. In some embodiments, an inner electrode may be formed by cutting the end of the wire to expose an electrically conductive cross-section of the wire. In some embodiments, flat wires rather than round wires are used to further reduce the crossing profile of the electrode assembly.

As shown in FIG. 4, the first inner electrode 430a is adjacent to, but not in contact with, a distal side edge 413 of the conductive sheath 412. The conductive sheath 412 functions as an outer electrode, and the inner electrode 430a is placed a controlled distance apart from the distal side edge 413 of the first conductive sheath to allow for a reproducible arc for a given voltage and current. The electrical arcs are then used to generate shock waves in the conductive fluid. In operation, a first shock wave is created across the inner electrode 430a and the distal side edge 413 of the conductive sheath 412. In a similar manner, a portion of the insulated wire 432 is removed to form a second inner electrode 432a. Specifically, a portion of the insulating layer of the wire 432 is removed near the proximal end of the wire 432 to expose an electrically conductive wire portion along the length of the wire, forming the second inner electrode 432a. As shown, the second inner electrode 432a is adjacent to, but not in contact with, a proximal side edge 411 of the conductive sheath 412. Further, the first inner electrode 430a and the second inner electrode 432a are positioned circumferentially 180 degrees from each other. In operation, the conductive sheath 412 acts as an outer electrode and a second shock wave is created across the second inner electrode 432a and the proximal side edge 411 of the first conductive sheath 412. The diagonal placement of the inner electrodes allows the sonic output to be distributed more evenly longitudinally along the balloon while making the shock waves less annular. One of ordinary skill in the art should recognize that the location of a shock wave can be configured in a flexible manner by arranging the corresponding wire and the corresponding conductive sheath (and the location of the corresponding cut-out on the sheath, if available) accordingly.

As described in assignee's prior filing U.S. Pub. No. 2019/0150960, two emitters can be formed along the same side edge of the sheath; further, a shock wave can be generated between an inner electrode and a straight side edge of the conductive sheath that does not include any cut-outs.

Figure 5:
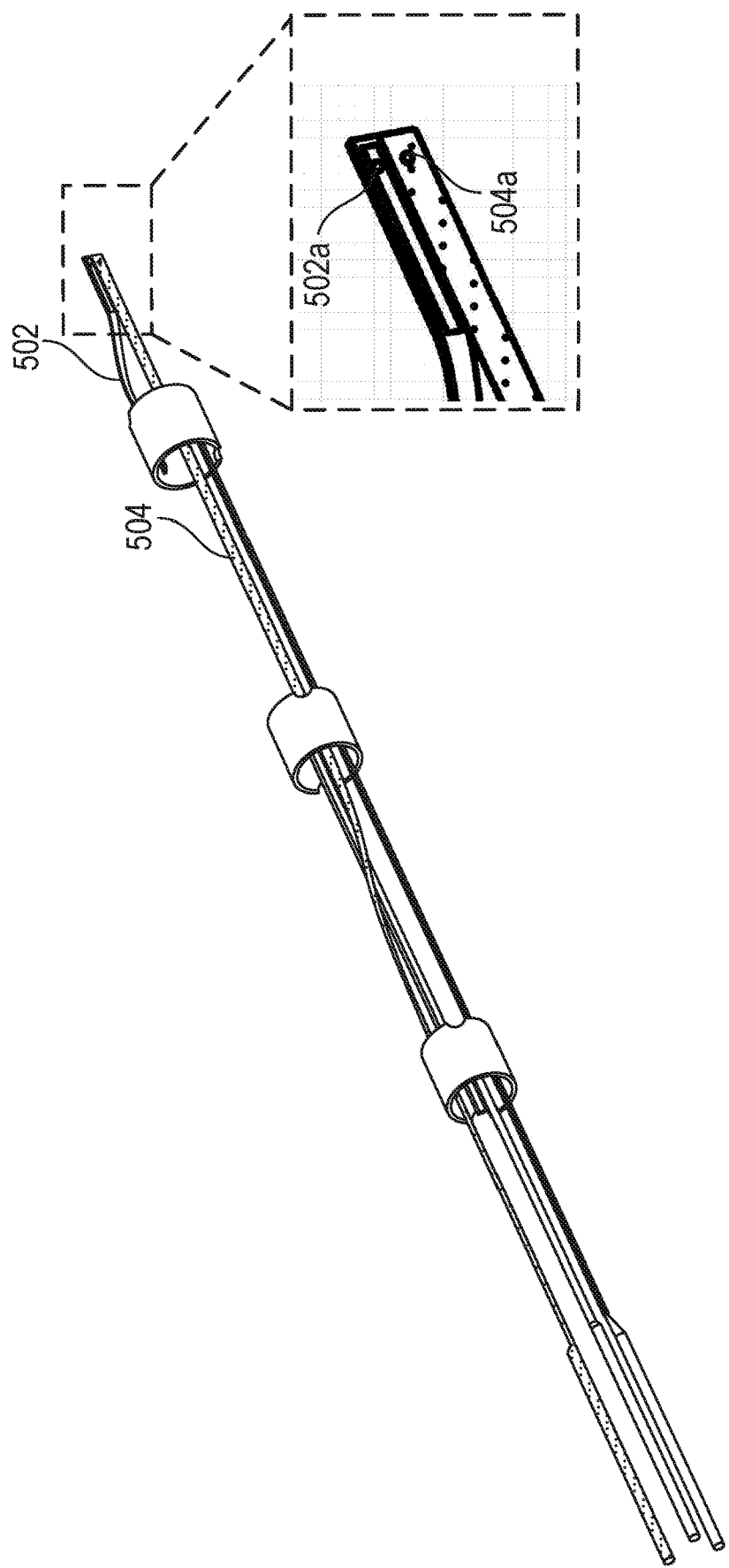
FIG. 5 depicts another exemplary set of shock wave electrode assemblies, in accordance with some embodiments.

An emitter can also be formed by the distal portions of two wires, as depicted in FIG. 5. A shown, a portion of the insulating layer of the wire 502 is removed near the distal end of the wire to expose an electrically conductive wire portion, forming an electrode 502a. Further, a portion of the insulating layer of the wire 504 is removed near the distal end of the wire to expose an electrically conductive wire portion, forming an electrode 504a. The pair of electrodes are adjacent to, but not in contact with, each other. Specifically, the pair of electrodes are placed a controlled distance apart to allow for a reproducible arc for a given voltage and current. The electrical arcs are then used to generate shock waves in the conductive fluid.

The wires 502 and 504 can be flattened to reduce the profile of the electrode pair. As shown in FIG. 5, while the proximal end of the wire 504 retains its original shape (i.e., cylindrical), the distal segment of the wire 504 has been flattened to reduce its profile. In some embodiments, a wire of 0.0053"-0.0064" in diameter can be flattened to 0.0030"-0.0040" in diameter, resulting in the flattened distal segment of the wire having a diameter that is approximately 47% to 75% relative to the diameter of the unflattened proximal segment of the wire. Having wires in the distal leg may affect the dimension and flexibility of the device, thus deliverability.

Figure 6:
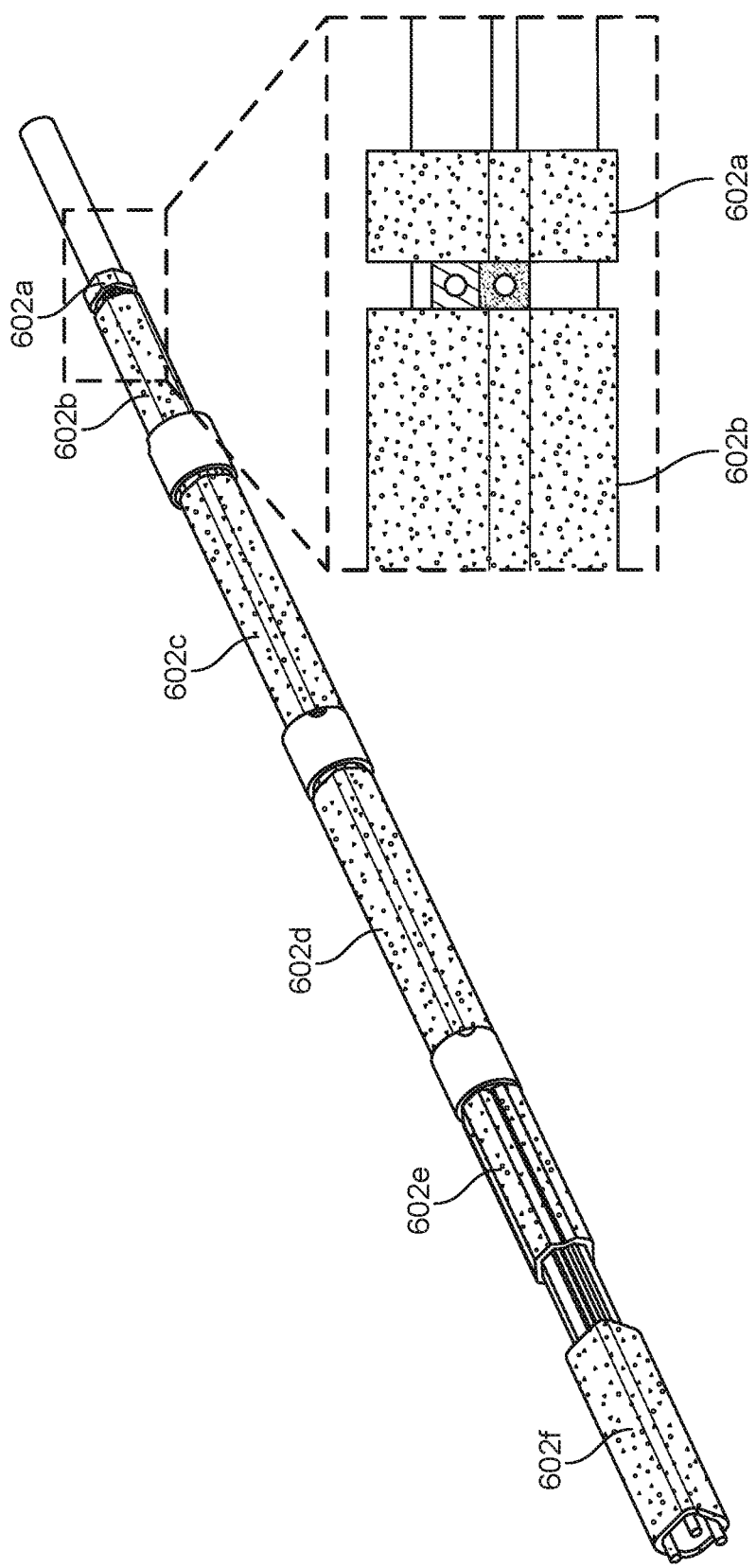
FIG. 6 depicts another exemplary set of shock wave electrode assemblies, in accordance with some embodiments.

In some embodiments, a layer of polyethylene terephthalate ("PET") can cover the wires before and after the cutouts to hold down the wires. As shown in FIG. 6, a plurality of PET bands 602a-f are used to secure the wires to the elongated tube. Specifically, PET bands 602a and 602b covers the two wires forming the distal electrode pair before and after the cutouts. In some embodiments, these cutouts are recessed from the top surface by 0.00025" (thickness of the PET).

Figure 1E:
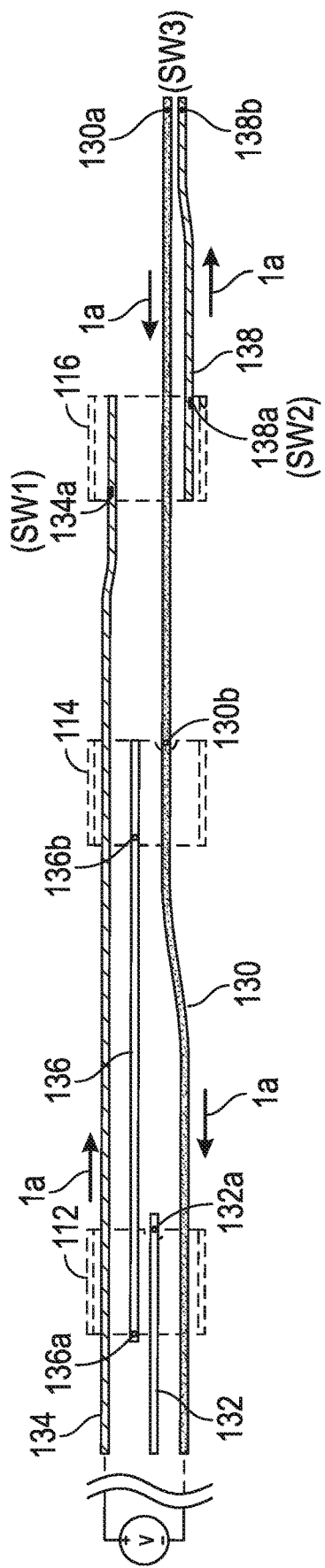
FIG. 1E schematically depicts an electrical diagram of the configuration of FIG. 1B, in accordance with some embodiments.
Figure 1F:
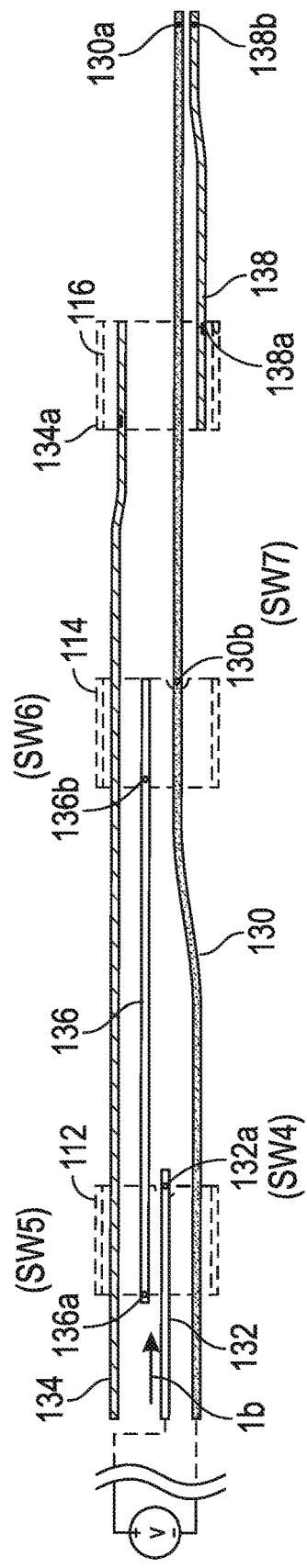
FIG. 1F schematically depicts an electrical diagram of the configuration of FIG. 1B, in accordance with some embodiments.

FIGS. 1E and 1F schematically depict two electrical diagrams of the configuration of FIGS. 1B-D, in accordance with some embodiments. With reference to FIG. 1E, when a first high voltage is applied (e.g., using the high voltage pulse generator 150 of FIG. 1B) across the proximal end of the insulated wire 130 and the proximal end of the insulated wire 134, a current 1a may flow as indicated by the arrows, with the insulated wire 130 as the common ground wire (i.e., connecting to a ground or negative channel). As shown, the current flows from the proximal end of the insulated wire 134 toward to the distal end of the insulated wire 134 and, via the insulation removed spot that is electrically conductive (i.e., inner electrode 134a), to the proximal side edge of the conductive sheath 116 (i.e., outer electrode). The duration and the magnitude of the voltage pulse are set to be sufficient to generate a gas bubble at the surface of the inner electrode 134a a causing a plasma arc of electric current to traverse the bubble and create a rapidly expanding and collapsing bubble, which creates the mechanical shock wave in the balloon ("SW1"). The size of the bubble and the rate of expansion and collapse of the bubble (and therefore the magnitude, duration, and distribution of the mechanical force) may vary based on the magnitude and duration of the voltage pulse, as well as the distance between the inner and outer electrodes, the surface area of the electrodes, and/or the shape of the outer electrode (e.g., whether there is an arcuate cut-out on the side edge).

The current 1a may further traverse from the distal side edge of the conductive sheath 116 (i.e., outer electrode) to the insulated wire 138, via the insulation removed spot near the proximal end of the insulated wire 138 (i.e., inner electrode 138a). The voltage pulse may create a potential difference high enough to form a plasma arc between them, generating a bubble that gives rise to a second shock wave ("SW2"). In the depicted example, the inner electrode 134a and the inner electrode 138a a are located circumferentially opposite to each other (e.g., 180 degrees apart around the circumference of the elongated tube), and thus the first shock wave and the second shock wave may propagate in opposite directions, extending outward from the side of the elongated tube.

The current 1a may further traverse to the distal end of the wire 138 and, via the insulation removed spot that is electrically conductive near the distal end of the wire 138 (i.e., the electrode 138b), to the insulation removed spot that is electrically conductive near the distal end of the wire 130 (i.e., the electrode 130a). The high voltage pulse generator may apply a voltage pulse such that the potential difference between the 138b and 130a is high enough to form a plasma arc between them, generating a bubble that gives rise to a third shock wave ("SW3"). Similar to the 1$^{st}$ and 2$^{nd}$ shockwaves, the shockwave propagates and extends outward from the 2 insulation removed spots 138b and 130a.

The current then returns to the voltage source generator via the insulated wire 130 to a voltage output port (not depicted), which may be a negative channel or a ground channel. Optionally, a connector (not depicted) may be provided between the insulated wires 134 and 130 and the voltage pulse generator so that the wires may be easily connected to the output ports of the high voltage generator.

With reference to FIG. 1F, when a second high voltage is applied (e.g., using the high voltage pulse generator 150 of FIG. 1B) across the proximal end of the insulated wire 130 and the proximal end of the insulated wire 132, a current 1b may flow as indicated by the arrows, with the insulated wire 130 as the common ground wire (i.e., connecting to a ground or negative channel). As shown, the current flows from the proximal end of the insulated wire 132 toward to the distal end of the insulated wire 132 and, via the insulation removed spot that is electrically conductive (i.e., inner electrode 132a), to the distal side edge of the conductive sheath 112 (i.e., outer electrode), generating shock waves ("SW4"). The current 1b may further traverse from the proximal side edge of the conductive sheath 112 (i.e., outer electrode) to the insulated wire 136, via the insulation removed spot near the proximal end of the insulated wire 136 (i.e., inner electrode 136a), generating shock waves ("SW5"). As shown, 132a and 136a are positioned circumferentially 180 degrees from each other on opposite edges of the conductive sheath 112.

The current 1b may further traverse toward the distal end of the wire 136 and, via the insulation removed spot that is electrically conductive near the distal end of the wire 136 (i.e., the electrode 136b), to the proximal side edge of conductive sheath 114, generating shock waves ("SW6"). The current 1b may further traverse from the distal side edge of the conductive sheath 114) to the insulated wire 130, via the insulation removed spot on the insulated wire 130 (i.e., inner electrode 130b), generating shock waves ("SW7"). The current then returns to the voltage source generator via the insulated wire 130 to a voltage output port. As shown, 136b and 130b are positioned circumferentially 180 degrees from each other on opposite edges of conductive sheath 114.

The current flows depicted in FIGS. 1E and 1F can occur simultaneously (e.g., by applying two voltage channels simultaneously) or at different times depending on the stage of the treatment. In the exemplary treatment discussed above, only current 1a is activated during the first stage of the treatment, thus activating only SW1, SW2, and SW3. This is to break loose calcifications in a tight lesion that only the distal segments (e.g., distal cone and/or distal leg) of the balloon can cross or come close to. After calcium in the tight lesion has been modified, the balloon is deflated and advanced further into the lesion. The balloon is again inflated to IVL pressure. In the second stage of the IVL treatment, all of the emitters are activated simultaneously. Shock waves generated by the proximal emitters (i.e., SW4, SW5, SW6, and SW7) provide additional treatment to the calcific lesion, while shock waves generated by the three distal emitters (i.e., SW1, SW2, SW3) allows further advancement of the balloon. Alternatively, only SW4, SW5, SW6, and SW7 are activated in the 2$^{nd}$ stage.

In some embodiments, a multiplexor may be used with the high voltage pulse generator to control application of pulses. This may allow shock waves with different frequency, magnitude, and timing to be generated along the elongated tube. In the depicted embodiment in FIG. 1E-F, the two voltage channels share the same common ground wire (i.e., insulated wire 130). One of ordinary skill in the art should understand that any number of voltage channels (e.g., 4) may be configured around a single elongated tube, and these voltage channels may rely on the same or different common ground wires.

FIGS. 2A-D depict another exemplary shock wave electrode assemblies 201 that can be included in the exemplary shock wave angioplasty device 100 of FIG. 1B, according to some embodiments of the invention. While the embodiment 101 in FIG. 1C includes only one wire-to-wire electrode pair (i.e., labelled "E1" in FIG. 1C), the embodiment 201 includes two wire-to-wire electrode pairs (labelled "E1" and "E2" in FIG. 2A). In some embodiments, both E1 and E2 are disposed within the leg segment of the balloon; in some embodiments, E1 is disposed within the leg segment while E2 is disposed within the cone segment of the balloon.

Comparing to the embodiment 101 in FIG. 1C, the embodiment 201 has a longer distal segment that is extremely low-profile (i.e., profile smaller than the cross section of a conductive sheath). Thus, when treating a calcified lesion that has a smaller opening than the conductive sheath, the embodiment 201 (when deflated) can allow both E1 and E2 to cross the opening and be advanced further into the lesion, thus a larger area of the calcified lesion to be broken down in the first stage of the treatment and allowing the procedure to be completed more efficiently.

Figure 2A:
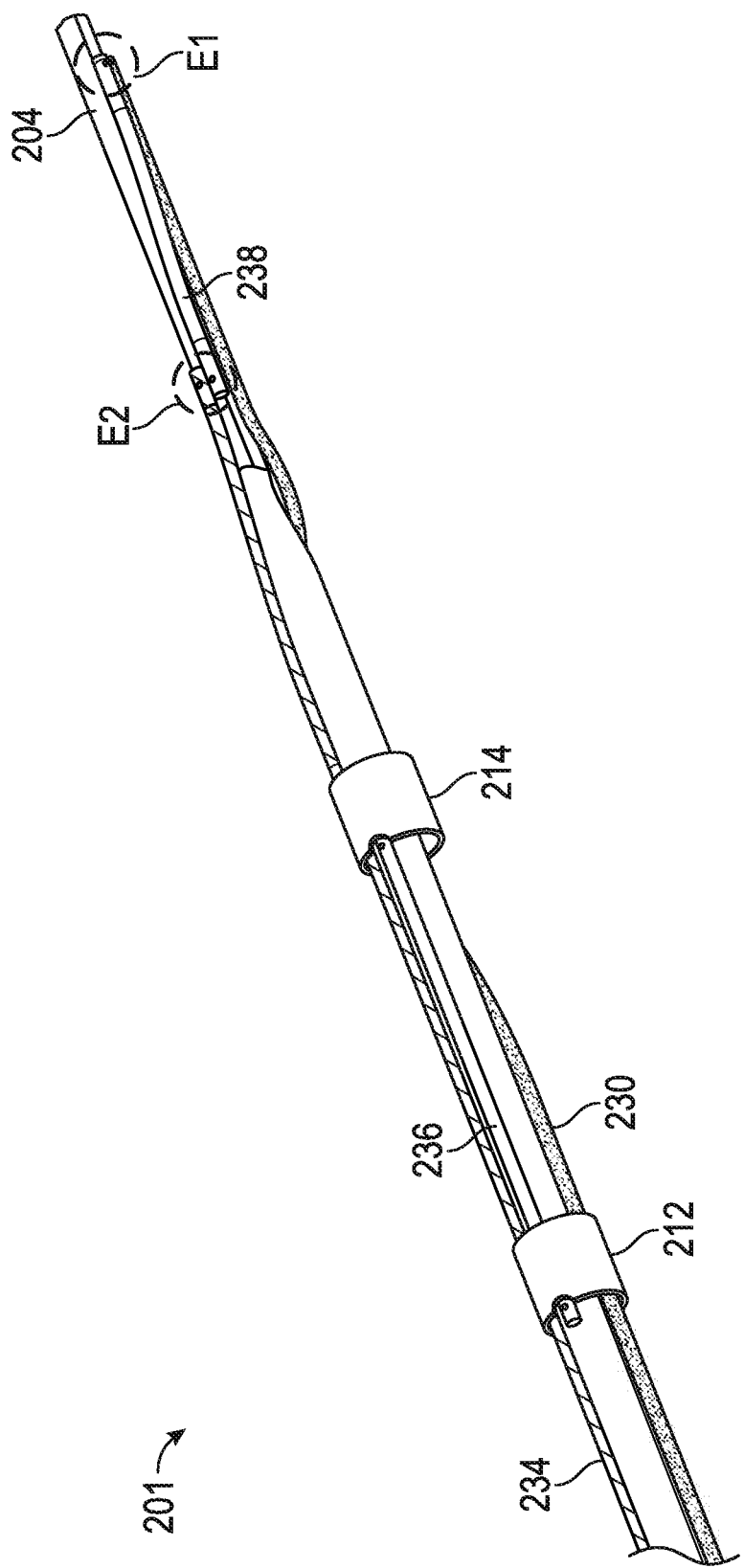
FIG. 2A depicts a set of shock wave electrode assemblies in an exemplary shock wave angioplasty device that may be activated to generate shock waves at multiple locations, in accordance with some embodiments.

With reference to FIG. 2A, an elongated tube 204 has a tapered distal portion. All wires are tacked down using adhesive. A layer of polymer, such as polyethylene terephthalate ("PET"), can cover the wires before and after the emitters/insulation removed spots to hold down the wires. A number of insulated wires (e.g., lead or interstation wires) 230, 234, 236, and 238 are disposed on the outer surface of the elongated tube 204 such that they extend along the length of the elongated tube. The wires can be straight or twisted. Further, two conductive sheaths 212 and 214 each circumferentially mounted around the elongated tube 204.

Figure 2B:
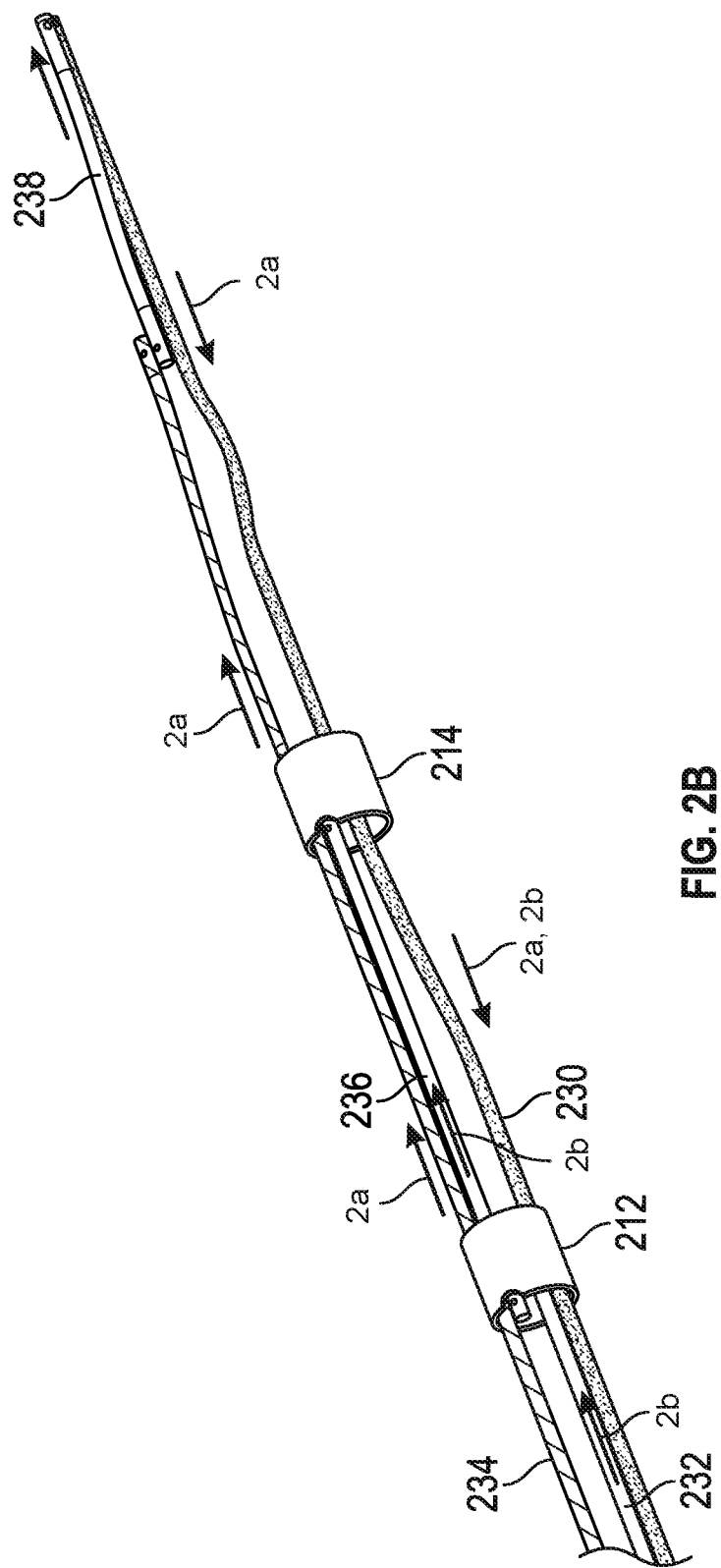
FIG. 2B depicts the connectivity between a plurality of inner electrodes and sheaths to attain the configuration of FIG. 2A, in accordance with some embodiments.

FIG. 2B depicts the relative placement of the wires and the conductive sheaths, with the elongated tube removed. FIG. 2B further depicts two current flows 2a and 2b for generating six sources of shock waves, as described with reference to FIGS. 2C and 2D.

Figure 2C:
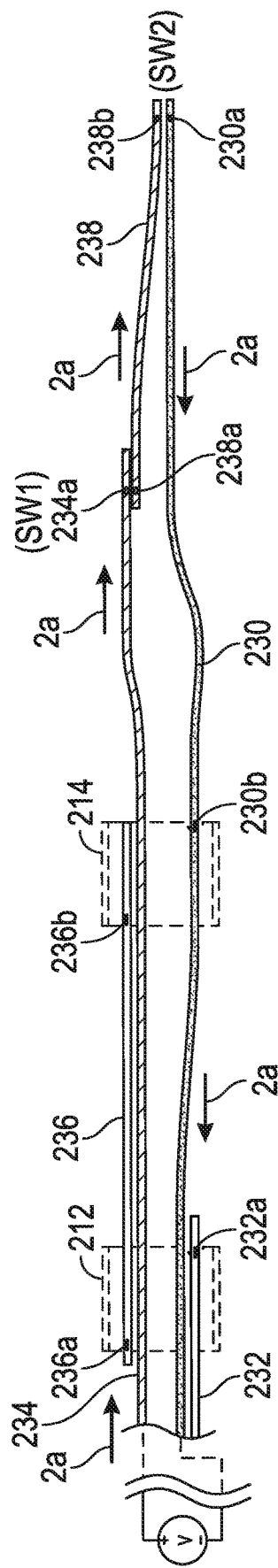
FIG. 2C schematically depicts an electrical diagram of the configuration of FIG. 2A, in accordance with some embodiments.
Figure 2D:
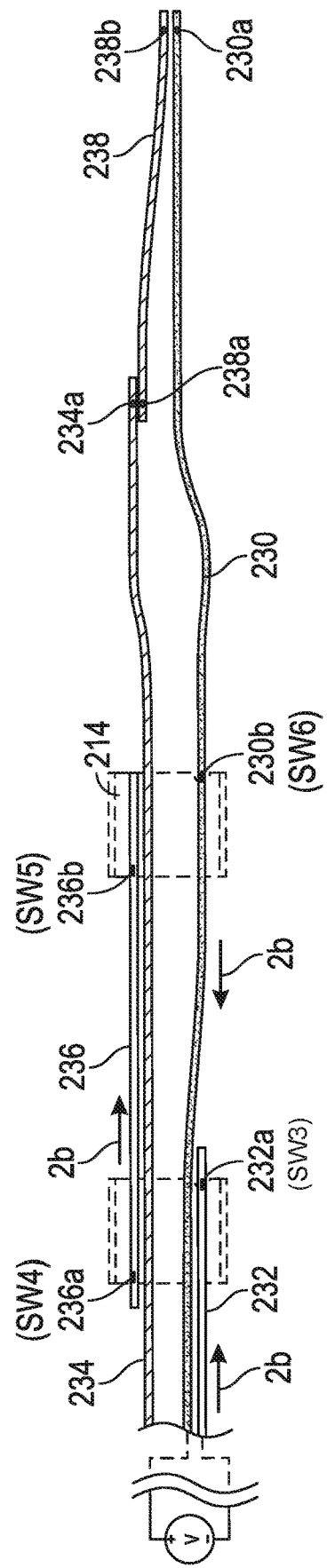
FIG. 2D schematically depicts an electrical diagram of the configuration of FIG. 2A, in accordance with some embodiments.

FIGS. 2C and 2D schematically depict two electrical diagrams of the configuration of FIGS. 2A-B, in accordance with some embodiments. With reference to FIG. 2C, when a first high voltage is applied (e.g., using the high voltage pulse generator 150 of FIG. 1B) across the proximal end of the insulated wire 230 and the proximal end of the insulated wire 234, a current 2a may flow as indicated by the arrows, with the insulated wire 230 as the common ground wire (i.e., connecting to a ground or negative channel). As shown, the current flows from the proximal end of the insulated wire 234 toward to the distal end of the insulated wire 234 and, via the insulation removed spot that is electrically conductive on wire 234 (i.e., electrode 234a), to the insulation removed spot that is electrically conductive on the proximal end of wire 238 (i.e., electrode 238a, generating shock waves ("SW1"). The shockwave propagates and extends outward from the 2 insulation removed spots 234a and 238a.

The current 2a may further traverse toward the distal end of wire 238 and, via the insulation removed spot near the distal end of the insulated wire 238 (i.e., electrode 238b), to the insulation removed spot near the distal end of the insulated wire 230 (i.e., electrode 230a), generating shock waves ("SW2"). The shockwave propagates and extends outward from the 2 insulation removed spots 238b and 230a. The current 2a then returns to the voltage source generator via the insulated wire 230 to a voltage output port (not depicted), which may be a negative channel or a ground channel. Optionally, a connector (not depicted) may be provided between the insulated wires 234 and 230 and the voltage pulse generator so that the wires may be easily connected to the output ports of the high voltage generator.

With reference to FIG. 2D, when a second high voltage is applied (e.g., using the high voltage pulse generator 150 of FIG. 1B) across the proximal end of the insulated wire 230 and the proximal end of the insulated wire 232, a current 2b may flow as indicated by the arrows, with the insulated wire 230 as the common ground wire (i.e., connecting to a ground or negative channel). As shown, the current flows from the proximal end of the insulated wire 232 toward to the distal end of the insulated wire 232 and, via the insulation removed spot that is electrically conductive (i.e., inner electrode 232a), to the distal side edge of the conductive sheath 212 (i.e., outer electrode), generating shock waves ("SW3"). The current 2b may further traverse from the proximal side edge of the conductive sheath 212 (i.e., outer electrode) to the insulated wire 236, via the insulation removed spot near the proximal end of the insulated wire 236 (i.e., inner electrode 236a), generating shock waves ("SW4"). As shown, 232a and 236a are positioned circumferentially 180 degrees from each other on opposite edges of the conductive sheath 212.

The current 2b may further traverse toward the distal end of the wire 236 and, via the insulation removed spot that is electrically conductive near the distal end of the wire 236 (i.e., the electrode 236b), to the proximal side edge of conductive sheath 214, generating shock waves ("SW5"). The current 2b may further traverse from the distal side edge of the conductive sheath 214) to the insulated wire 230, via the insulation removed spot on the insulated wire 230 (i.e., inner electrode 230b), generating shock waves ("SW6"). The current then returns to the voltage source generator via the insulated wire 230 to a voltage output port. As shown, 236b and 230b are positioned circumferentially 180 degrees from each other on opposite edges of conductive sheath 214.

The current flows depicted in FIGS. 2C and 2D can occur simultaneously (e.g., by applying two voltage channels simultaneously) or at different times depending on the stage of the treatment. In the exemplary treatment discussed above, only current 2a is activated during the first stage of the treatment, thus activating only SW1, and SW2. This is to break loose calcifications in a tight lesion that only the distal segments (e.g., distal cone and/or distal leg) of the balloon can cross or come close to. After calcium in the tight lesion has been modified, the balloon is deflated and advanced further into the lesion. The balloon is again inflated to IVL pressure. In the second stage of the IVL treatment, all of the emitters are activated simultaneously as shown in FIGS. 2C and 2D. Shock waves generated by the proximal emitters (i.e., SW3, SW4, SW5, SW6) provide additional treatment to the calcific lesion, while shock waves generated by the two distal emitters (i.e., SW1, SW2) allows further advancement of the balloon. Alternatively, only SW3, SW4, SW5, and SW6 are activated in the $2^{nd}$ stage.

FIGS. 3A-D depict another exemplary shock wave electrode assemblies 301 that can be included in the exemplary shock wave angioplasty device 100 of FIG. 1B, according to some embodiments of the invention. Unlike embodiment 101 and embodiment 201, the embodiment 301 does not include any wire-to-wire electrode pairs. Rather, all emitters are formed by a side edge of a conductive sheath and a conductive portion of a wire. Further, the two most distal emitters (formed at the two side edges of the conductive sheath 316) are both disposed in the cone segment ("M") of a balloon.

Figure 3A:
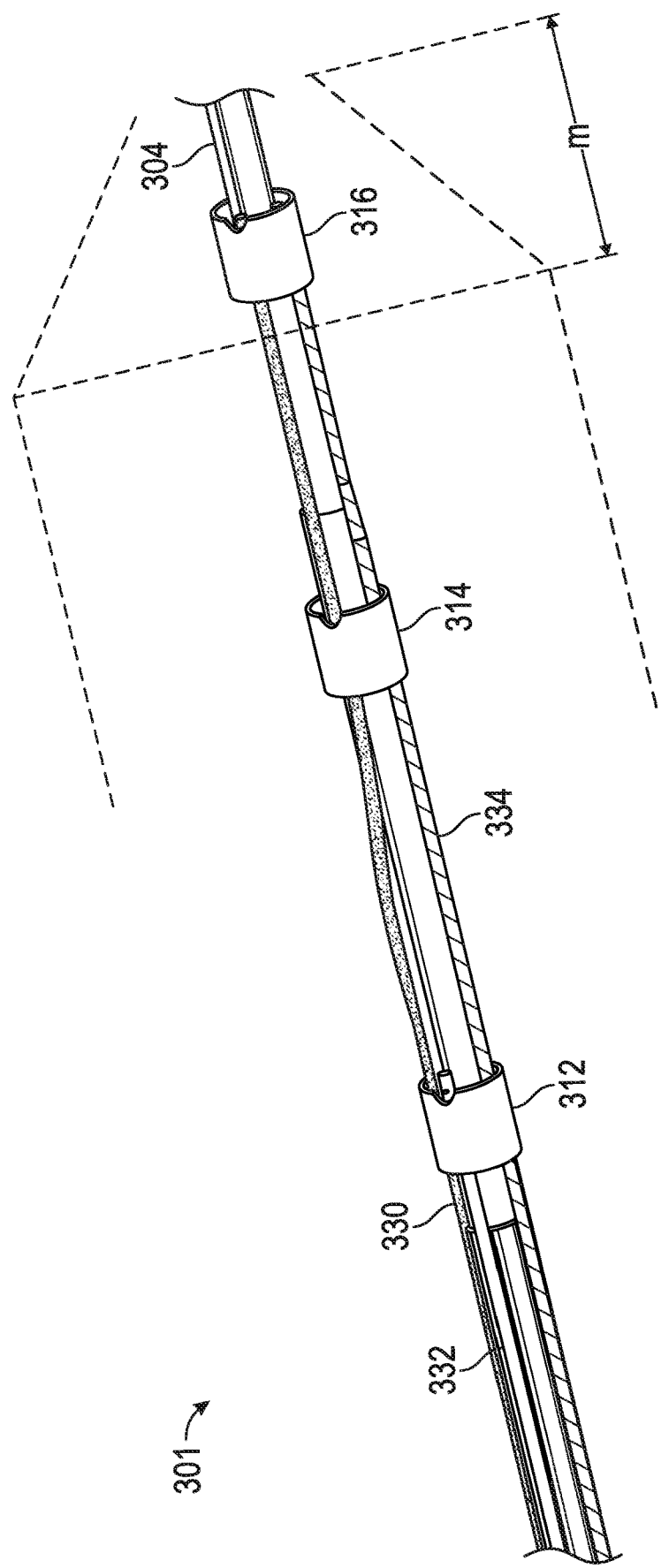
FIG. 3A depicts a set of shock wave electrode assemblies in an exemplary shock wave angioplasty device that may be activated to generate shock waves at multiple locations, in accordance with some embodiments.

With reference to FIG. 3A, a number of insulated wires (e.g., lead or interstation wires) 330, 332, 334 and 336 are disposed on the outer surface of the elongated tube 304 such that they extend along the length of the elongated tube. The wires can be straight or twisted. Further, three conductive sheaths 312, 314, and 316 each circumferentially mounted around the elongated tube 304.

Figure 3B:
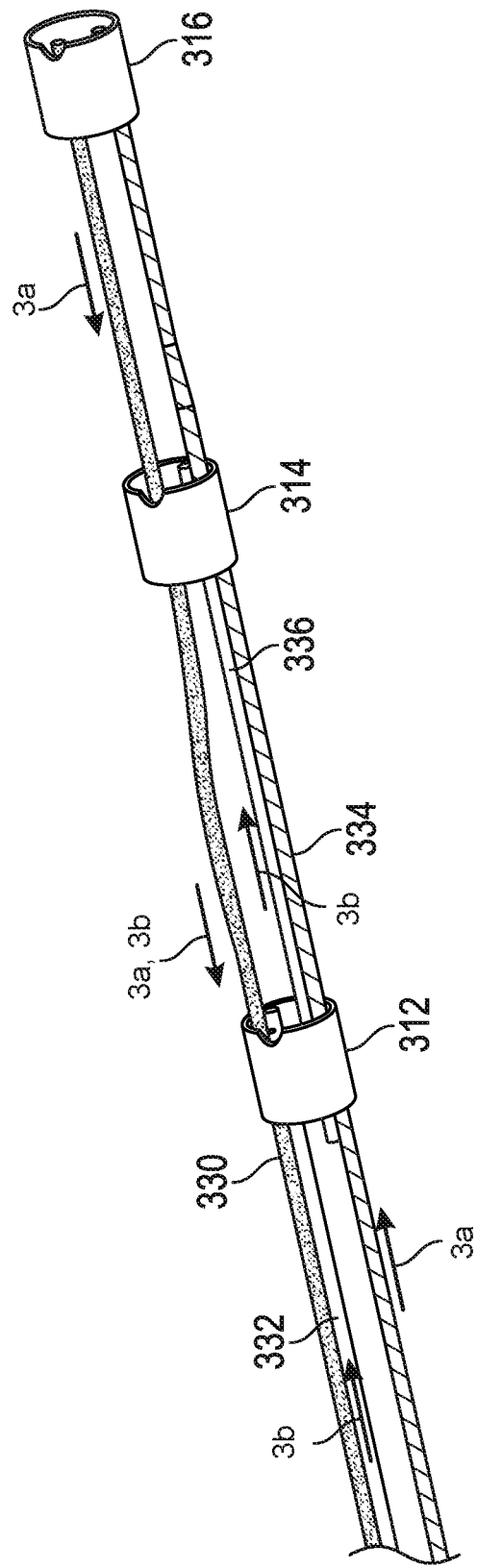
FIG. 3B depicts the connectivity between a plurality of inner electrodes and sheaths to attain the configuration of FIG. 3A, in accordance with some embodiments.

FIG. 3B depicts the relative placement of the wires and the conductive sheaths, with the elongated tube removed. FIG. 3B further depicts two current flows 3a and 3b for generating six sources of shock waves, as described with reference to FIGS. 3C and 3D.

Figure 3C:
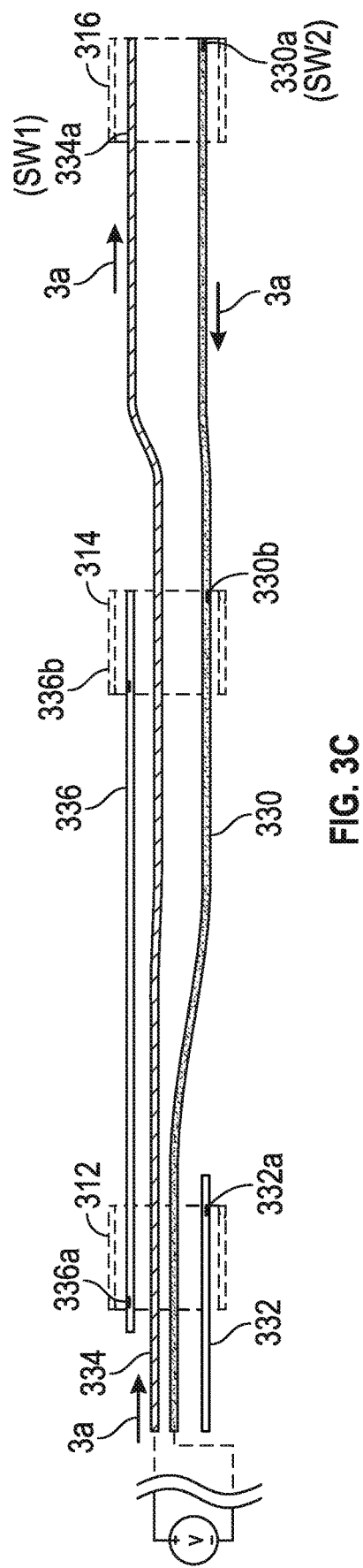
FIG. 3C schematically depicts an electrical diagram of the configuration of FIG. 3A, in accordance with some embodiments.
Figure 3D:
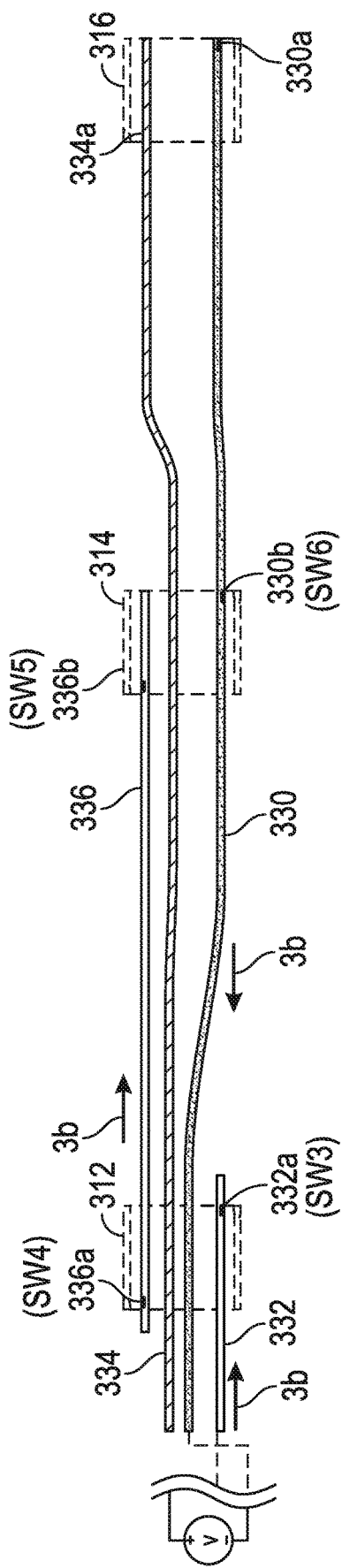
FIG. 3D schematically depicts an electrical diagram of the configuration of FIG. 3A, in accordance with some embodiments.

FIGS. 3C and 3D schematically depict two electrical diagrams of the configuration of FIGS. 3A-B, in accordance with some embodiments. With reference to FIG. 3C, when a first high voltage is applied (e.g., using the high voltage pulse generator 150 of FIG. 1B) across the proximal end of the insulated wire 330 and the proximal end of the insulated wire 334, a current 3a may flow as indicated by the arrows, with the insulated wire 330 as the common ground wire (i.e., connecting to a ground or negative channel). As shown, the current flows from the proximal end of the insulated wire 334 toward to the distal end of the insulated wire 334 and, via the insulation removed spot that is electrically conductive on wire 334 (i.e., electrode 334a), to the proximal side edge of the conductive sheath 316, generating shock waves ("SW1").

The current 3a may further traverse from the distal side edge of the conductive sheath 316 and, via the insulation removed spot near the distal end of the insulated wire 330 (i.e., electrode 330a), to the wire 330, generating shock waves ("SW2"). The current 3a then returns to the voltage source generator via the insulated wire 330 to a voltage output port (not depicted), which may be a negative channel or a ground channel. Optionally, a connector (not depicted) may be provided between the insulated wires 334 and 330 and the voltage pulse generator so that the wires may be easily connected to the output ports of the high voltage generator.

With reference to FIG. 3D, when a second high voltage is applied (e.g., using the high voltage pulse generator 150 of FIG. 1B) across the proximal end of the insulated wire 330 and the proximal end of the insulated wire 332, a current 3b may flow as indicated by the arrows, with the insulated wire 330 as the common ground wire (i.e., connecting to a ground or negative channel). As shown, the current flows from the proximal end of the insulated wire 332 toward to the distal end of the insulated wire 332 and, via the insulation removed spot that is electrically conductive (i.e., inner electrode 332a), to the distal side edge of the conductive sheath 312 (i.e., outer electrode), generating shock waves ("SW3"). The current 2b may further traverse from the proximal side edge of the conductive sheath 312 (i.e., outer electrode) to the insulated wire 336, via the insulation removed spot near the proximal end of the insulated wire 336 (i.e., inner electrode 336a), generating shock waves ("SW4"). As shown, 332a and 336a are positioned circumferentially 180 degrees from each other on opposite edges of the conductive sheath 312.

The current 3b may further traverse toward the distal end of the wire 336 and, via the insulation removed spot that is electrically conductive near the distal end of the wire 336 (i.e., the electrode 336b), to the proximal side edge of conductive sheath 314, generating shock waves ("SW5"). The current 3b may further traverse from the distal side edge of the conductive sheath 314) to the insulated wire 330, via the insulation removed spot on the insulated wire 330 (i.e., inner electrode 330b), generating shock waves ("SW6"). The current then returns to the voltage source generator via the insulated wire 330 to a voltage output port. As shown, 336b and 330b are positioned circumferentially 180 degrees from each other on opposite edges of conductive sheath 314.

The current flows depicted in FIGS. 3C and 3D can occur simultaneously (e.g., by applying two voltage channels simultaneously) or at different times depending on the stage of the treatment. In the exemplary treatment discussed above, only current 3a is activated during the first stage of the treatment, thus activating only SW1, and SW2. This is to break loose calcifications in a tight lesion that only the distal segments (e.g., distal cone and/or distal leg) of the balloon can cross or come close to. After calcium in the tight lesion has been modified, the balloon is deflated and advanced further into the lesion. The balloon is again inflated to IVL pressure. In the second stage of the IVL treatment, all of the emitters are activated simultaneously as shown in FIGS. 3C and 3D. Shock waves generated by the proximal emitters (i.e., SW3, SW4, SW5, SW6) provide additional treatment to the calcific lesion, while shock waves generated by the three distal emitters (i.e., SW1, SW2) allows further advancement of the balloon.

It will be understood that the foregoing is only illustrative of the principles of the invention, and that various modifications, alterations and combinations can be made by those skilled in the art without departing from the scope and spirit of the invention. Any of the variations of the various shock wave devices disclosed herein can include features described by any other shock wave devices or combination of shock wave devices herein. Furthermore, any of the methods can be used with any of the shock wave devices disclosed. Accordingly, it is not intended that the invention be limited, except as by the appended claims. For all of the variations described above, the steps of the methods need not be performed sequentially

The invention claimed is:

1. A device for generating shock waves, the device comprising:
   an elongated tube;
   a balloon wrapped circumferentially around a portion of the elongated tube, the balloon comprising:
      a distal end sealed to the elongated tube,
      a leg segment proximal to and extending directly from the distal end of the balloon,
      a cone segment proximal to and extending directly from the leg segment of the balloon, and
      a straight segment proximal to the cone segment of the balloon,
      wherein, when the balloon is inflated: the leg segment is of a tapered shape with an average diameter, the cone segment is of a tapered shape with an average diameter greater than the average diameter of the leg segment, and the straight segment is of a substantially cylindrical shape with a diameter greater than the average diameter of the cone segment; and
   a plurality of distal emitters configured to generate shock waves, wherein the plurality of distal emitters comprises at least two distal emitters positioned in the cone segment of the balloon, each of the at least two distal emitters positioned in the cone segment configured to generate shock waves such that shockwaves are generated at at least two different locations in the cone segment of the balloon, and wherein the plurality of distal emitters comprise at least one distal emitter positioned in the leg segment of the balloon.

2. The device of claim 1, wherein the plurality of distal emitters comprises at least one distal emitter located between approximately 0.5 mm and approximately 1 mm from a distal end of a gap between the leg segment of the balloon and the elongated tube.

3. The device of claim 1, wherein, when the balloon is inflated, a gap between an inner diameter of the leg segment and an outer diameter of the elongated tube is between around 0.001" to around 0.003".

4. The device of claim 1, wherein the leg segment is less than approximately 3.5 mm long, and wherein the cone segment is approximately 4.5 mm to approximately 5.5 mm long.

5. The device of claim 1, wherein, when the balloon is inflated, a first vertex angle between the leg segment of the balloon and the elongated tube is smaller than 5 degrees.

6. The device of claim 5, wherein, when the balloon is inflated, a second vertex angle between the cone segment of the balloon and the elongated tube is larger than the first vertex angle.

7. The device of claim 1, wherein the plurality of distal emitters comprises a first electrode pair, the first electrode pair comprising:
   a conductive portion of a first insulated wire; and
   a conductive portion of a second insulated wire.

8. The device of claim 7, wherein the conductive portion of the first insulated wire is formed by removing a first portion of insulation from the first insulated wire, and wherein the conductive portion of the second insulated wire is formed by removing a second portion of insulation from the second insulated wire.

9. The device of claim 8, wherein the first insulated wire comprises a flattened distal segment, and the first portion of insulation is removed from the flattened distal segment of the first insulated wire, and wherein the second insulated wire comprises a flattened distal segment, and the second portion of insulation is removed from the flattened distal segment of the second insulated wire.

10. The device of claim 9, wherein a diameter of the flattened distal segment of the first insulated wire is approximately 47% to 75% of a diameter of a proximal segment of the first insulated wire, and wherein a diameter of the flattened distal segment of the second insulated wire is approximately 47% to 75% of a diameter of a proximal segment of the second insulated wire.

11. The device of claim 7, wherein a layer of polymer covers at least a portion of the first insulated wire and the second insulated wire, such that the conductive portion of the first insulated wire is held a controlled distance apart from the conductive portion of the second insulated wire.

12. The device of claim 7, wherein the plurality of distal emitters further comprises a second electrode pair, the second electrode pair comprising:
   a further conductive portion of the second insulated wire; and
   a conductive portion of a third insulated wire.

13. The device of claim 7, wherein the plurality of distal emitters further comprises a second electrode pair and a third electrode pair, wherein the second electrode pair comprises:
   a further conductive portion of the second insulated wire; and
   a first side edge of a conductive sheath wrapped circumferentially around the elongated tube; and
   wherein the third electrode pair comprises:

a second side edge of the conductive sheath; and
a conductive portion of a third insulated wire.

14. The device of claim 1, wherein the plurality of distal emitters comprises a first electrode pair and a second electrode pair, wherein the first electrode pair comprises:
   a conductive portion of a first insulated wire; and
   a first side edge of a conductive sheath wrapped circumferentially around the elongated tube; and
wherein the second electrode pair comprises:
   a second side edge of the conductive sheath; and
   a conductive portion of a second insulated wire.

15. The device of claim 14, wherein the first side edge and the second side edge are positioned circumferentially 180 degrees on opposite edges of the conductive sheath.

16. The device of claim 1, wherein the elongated tube is tapered toward the distal end.

17. The device of claim 1, further comprising:
   at least one proximal emitter configured to generate shock waves, wherein the at least one proximal emitter is positioned in the straight segment of the balloon.

18. The device of claim 17, further comprising a variable high voltage pulse generator selectively connected to the plurality of distal emitters and the at least one proximal emitter, wherein the variable high voltage pulse generator can be activated to generate shock waves at either the plurality of distal emitters or the at least one proximal emitter.

\* \* \* \* \*